US011724005B2

(12) United States Patent
Kuwahara et al.

(10) Patent No.: US 11,724,005 B2
(45) Date of Patent: Aug. 15, 2023

(54) METHOD FOR MANUFACTURING CILIARY MARGIN STEM CELLS

(71) Applicants: SUMITOMO CHEMICAL COMPANY, LIMITED, Tokyo (JP); RIKEN, Wako (JP)

(72) Inventors: Atsushi Kuwahara, Osaka (JP); Yoshiki Sasai, Kobe (JP)

(73) Assignees: SUMITOMO CHEMICAL COMPANY, LIMITED, Tokyo (JP); RIKEN, Wako (JP)

( * ) Notice: Subject to any disclaimer, the term of this patent is extended or adjusted under 35 U.S.C. 154(b) by 281 days.

(21) Appl. No.: 15/112,187

(22) PCT Filed: Oct. 16, 2014

(86) PCT No.: PCT/JP2014/077603
§ 371 (c)(1),
(2) Date: Jul. 17, 2016

(87) PCT Pub. No.: WO2015/107738
PCT Pub. Date: Jul. 23, 2015

(65) Prior Publication Data
US 2017/0319748 A1 Nov. 9, 2017

(30) Foreign Application Priority Data
Jan. 17, 2014 (JP) .................. 2014-006464

(51) Int. Cl.
*A61L 27/38* (2006.01)
*A61K 35/545* (2015.01)
*C12N 5/079* (2010.01)
*A61K 35/30* (2015.01)

(52) U.S. Cl.
CPC ........ *A61L 27/3878* (2013.01); *A61K 35/545* (2013.01); *A61L 27/383* (2013.01); *A61L 27/3834* (2013.01); *A61L 27/3895* (2013.01); *C12N 5/0621* (2013.01); *A61K 35/30* (2013.01); *A61L 2400/06* (2013.01); *A61L 2430/16* (2013.01); *C12N 2501/10* (2013.01); *C12N 2501/11* (2013.01); *C12N 2501/115* (2013.01); *C12N 2501/155* (2013.01); *C12N 2501/385* (2013.01); *C12N 2501/41* (2013.01); *C12N 2501/415* (2013.01); *C12N 2501/727* (2013.01); *C12N 2501/999* (2013.01); *C12N 2506/02* (2013.01)

(58) Field of Classification Search
None
See application file for complete search history.

(56) References Cited

U.S. PATENT DOCUMENTS

| 7,312,025 B2 | 12/2007 | Kubota et al. |
| 2004/0197317 A1 | 10/2004 | Rao et al. |
| 2005/0048041 A1 | 3/2005 | Rao et al. |
| 2007/0107071 A1* | 5/2007 | Couillard-Despres ........ A01K 67/0278 800/14 |
| 2008/0044901 A1 | 2/2008 | Sasai et al. |
| 2009/0170148 A1* | 7/2009 | Smirnova ............ C12N 5/0621 435/29 |
| 2011/0091869 A1 | 4/2011 | Sasai et al. |
| 2013/0330302 A1* | 12/2013 | Temple ................ C12N 5/0619 424/93.7 |
| 2014/0341864 A1 | 11/2014 | Nakano et al. |
| 2015/0132787 A1 | 5/2015 | Sasai et al. |
| 2016/0376554 A1 | 12/2016 | Kuwahara et al. |

FOREIGN PATENT DOCUMENTS

| EP | 2554662 A1 | 2/2013 |
| EP | 3081637 A1 | 10/2016 |
| JP | 2012-245007 A | 12/2012 |
| KR | 10-2006-0002745 A | 1/2006 |
| WO | WO 2009/148170 A1 | 12/2009 |
| WO | WO 2012/173207 A1 | 12/2010 |
| WO | WO 2013/077425 A1 | 5/2013 |
| WO | WO 2013/183774 A1 | 12/2013 |
| WO | WO 2015/087614 A1 | 6/2015 |

OTHER PUBLICATIONS

Lord-Grignon et al., Identification of genes expressed in retinal progenitor/stem cell colonies isolated from the ocular ciliary body of adult mice. Gene Expression Patterns, 2006. 6: 992-999.*
Nakano et al., "Self-Formation of Optic Cups and Storable Stratified Neural Retina from Human ESCs," *Cell Stem Cell*, 10(6): 771-785 (2012).
Aleksandrova et al., "Structure and Cell Composition of Spheres Cultured from Human Fetal Retina," *Bull. Exp. Biol. Med.*, 142(1): 152-159 (2006).
Eiraku et al., "Self-organizing optic-cup morphogenesis in three-dimensional culture," *Nature*, 472(7341): 51-56 (2011).
Shirai et al., "Transplantation of human embryonic stem cell-derived retinal tissue in two primate models of retinal degeneration," *Proc. Natl. Acad. Sci. U.S.A.*, 113(1): E81-E90 (2015).
European Patent Office, Extended European Search Report in European Patent Application No. 14878653.6 (Sep. 15, 2017).

(Continued)

*Primary Examiner* — James D Schultz
(74) *Attorney, Agent, or Firm* — Leydig, Voit & Mayer, Ltd.

(57) ABSTRACT

The invention provides a method for producing a ciliary marginal zone stem cell induced to differentiate from a pluripotent stem cell, including either the following step (1) or step (2), or both of these steps: (1) a step of floating culturing cells obtained from a cell aggregate containing a ciliary marginal zone-like structure induced to differentiate from pluripotent stem cells, thereby obtaining a retinosphere; and (2) a step of collecting stage specific embryonic antigen-1 positive cells from cells obtained from a cell aggregate containing a ciliary marginal zone-like structure induced to differentiate from pluripotent stem cells.

11 Claims, 9 Drawing Sheets

(56) References Cited

OTHER PUBLICATIONS

Ahmad et al., "Identification of Neural Progenitors in the Adult Mammalian Eye," *Biochem. Biophys. Res. Commun.*, 270(2): 517-521 (2000).
Bahrami et al., "Isolation and Expansion of Endothelial Progenitor Cells Derived from Mouse Embryonic Stem Cells," *Methods Mol. Biol.*, 916: 81-96 (2012).
Centanin et al., "Fate Restriction and Multipotency in Retinal Stem Cells," *Cell Stem Cell*, 9(6): 553-562 (2011).
Coles et al., "Facile isolation and the characterization of human retinal stem cells," *Proc. Natl. Acad. Sci. U.S.A.*, 101(44): 15772-15777 (2004).
El Yakoubi et al., "Hes4 Controls Proliferative Properties of Neural Stem Cells During Retinal Ontogenesis," *Stem Cells*, 30(12): 2784-2795 (2012).
Fischer et al., "The ciliary marginal zone (CMZ) in development and regeneration of the vertebrate eye," *Exp. Eye Res.*, 116: 199-204 (2013).
Hirami et al., "Generation of retinal cells from mouse and human induced pluripotent stem cells," *Neurosci. Lett.*, 458(3): 126-131 (2009).
Huang et al., "Isolation and Functional Characterization of Pluripotent Stem Cell-Derived Cardiac Progenitor Cells," *Curr. Protoc. Stem Cell Biol.*, 1F.10(Supplement 14): 1F.10.1-1F.10.14 (2010).
Koso et al., "SSEA-1 marks regionally restricted immature subpopulations of embryonic retinal progenitor cells that are regulated by the Wnt signaling pathway," *Dev. Biol.*, 292(1): 265-276 (2006).
Koso et al., "CD138/Syndecan-1 and SSEA-1 Mark Distinct Populations of Developing Ciliary Epithelium That Are Regulated Differentially by Wnt Signal," *Stem Cells*, 26(12): 3162-3171 (2008).
Kubo et al., "Wnt2b controls retinal cell differentiation at the ciliary marginal zone," *Development*, 130(3): 587-598 (2003).
Kubo et al., "Hairy1 acts as a node downstream of Wnt signaling to maintain retinal stem cell-like progenitor cells in the chick ciliary marginal zone," *Development*, 136(11): 1823-1833 (2009).
Moshiri et al., "Retinal stem cells and regeneration," *Int. J. Dev. Biol.*, 48: 1003-1014 (2004).
Panchision et al., "Optimized Flow Cytometric Analysis of Central Nervous System Tissue Reveals Novel Functional Relationships Among Cells Expressing CD133, CD15, and CD24," *Stem Cells*, 25(6): 1560-1570 (2007).
Raymond et al., "Molecular characterization of retinal stem cells and their niches in adult zebrafish," *BMC Dev. Biol.*, 6: 36 (2006).
Stephens et al., "Loss of *adenomatous polyposis coli* (*apc*) Results in an Expanded Ciliary Marginal Zone in the Zebrafish Eye," *Dev. Dyn.*, 239(7): 2066-2077 (2010).
Tropepe et al., "Retinal Stem Cells in the Adult Mammalian Eye," *Science*, 287(5460): 2032-2036 (2000).
Wehman et al., "Genetic dissection of the zebrafish retinal stem-cell compartment," *Dev. Biol.*, 281(1): 53-65 (2005).
Intellectual Property Office of Singapore, Search Report in Singaporean Patent Application 11201605833P (dated Jul. 10, 2017).
Japanese Patent Office, International Search Report in International Patent Application No. PCT/JP2014/077603 (dated Jan. 13, 2015).
Giordano et al., "Fibroblast growth factor and epidermal growth factor differently affect differentiation of murine retinal stem cells in vitro," *Mol. Vis.*, 13: 1842-1850 (2007).

\* cited by examiner p<0.01, *p<0.001.
ANOVA followed by post-hoc Tukey's test.

METHOD FOR MANUFACTURING CILIARY MARGIN STEM CELLS

CROSS-REFERENCE TO RELATED APPLICATIONS

This patent application is the U.S. national phase of International Patent Application No. PCT/JP2014/077603, filed Oct. 16, 2014, which claims the benefit of Japanese Patent Application No. 2014-006464, filed on Jan. 17, 2014, which are incorporated by reference in their entireties herein.

TECHNICAL FIELD

The present invention relates to a method for producing a ciliary marginal zone stem cell, and so on.

BACKGROUND ART

A tissue stem cell having differentiation potency into a retinal cell and self-replication ability is expected to be applicable to a cell transplantation treatment, a drug discovery screening and so on.

The ciliary marginal zone (CMZ) of the in vivo retina is known to perform important functions for the structural formation and maintenance of retinal tissues (see, for example, non-patent document 1). A stem cell of a retinal tissue (retinal stem cell) having differentiation potency into a retinal cell such as photoreceptor cell is present in a ciliary marginal zone (see, for example, non-patent document 2). Rdh10 gene (non-patent document 3) and Otx1 gene (non-patent document 1) are known as gene markers of the ciliary marginal zone.

When a cell aggregate comprising a retinal tissue that can be formed by suspension culture of pluripotent stem cells is further cultured under particular conditions, a cell aggregate comprising a ciliary marginal zone-like structure is obtained (see, for example, patent document 1). In such "cell aggregate comprising a ciliary marginal zone-like structure", the ciliary marginal zone-like structure functions as a progress zone, and there can be formed with high frequency a continuous neural retina having a layer structure adjacent to the ciliary marginal zone-like structure. The "progress zone" is a population of undifferentiated cells localized in a part of a tissue, and is a population of cells having properties to continuously proliferate in the process of development and regeneration to contribute to the growth of a tissue as a whole and/or properties to contribute to the growth of the surrounding tissues by secreting a growth factor and so on.

DOCUMENT LIST

Patent Document patent document 1: WO 2013/183774 A1

Non-Patent Documents non-patent document 1: DEVELOPMENTAL DYNAMICS, Volume: 239, Pages: 2066-2077 (2010)
non-patent document 2: Proc. Natl. Acad. Sci. USA, Volume: 101, Pages: 15772-15777 (2004)
non-patent document 3: Development, Volume: 136, Pages: 1823-1833 (2009)

SUMMARY OF THE INVENTION

Problems to be Solved by the Invention

The development of a method for producing a tissue stem cell having differentiation potency into a retinal cell and self-replication ability efficiently with a high purity has been desired.

Means of Solving the Problems

The present invention provides a method of producing a cell having differentiation potency into a retinal cell such as photoreceptor cell and self-replication ability, present in a cell aggregate comprising a ciliary marginal zone-like structure, which was induced to differentiate from pluripotent stem cells (hereinafter sometimes referred to as a ciliary marginal zone stem cell or CMZ stem cell), and so on.

[1] A method for producing a ciliary marginal zone stem cell induced to differentiate from a pluripotent stem cell, comprising either the following step (1) or step (2), or both of these steps (hereinafter sometimes referred to as the stem cell production method 1 of the present invention):

(1) a step of floating culturing cells obtained from a cell aggregate comprising a ciliary marginal zone-like structure induced to differentiate from pluripotent stem cells, thereby obtaining a retinosphere; and (2) a step of collecting stage specific embryonic antigen-1 (hereinafter sometimes referred to as SSEA-1) positive cells from cells obtained from a cell aggregate comprising a ciliary marginal zone-like structure induced to differentiate from pluripotent stem cells;

[2] the method according to the above-mentioned [1], wherein the step (1) is performed, and wherein the "cells obtained from a cell aggregate comprising a ciliary marginal zone-like structure induced to differentiate from pluripotent stem cells" are cells obtained by dispersing:
a cell aggregate comprising a ciliary marginal zone-like structure induced to differentiate from pluripotent stem cells, or
a ciliary marginal zone-like structure separated from the cell aggregate (hereinafter sometimes referred to as the stem cell production method 2 of the present invention);

[3] the method according to the above-mentioned [1], wherein the step (2) is performed, and wherein the "cells obtained from a cell aggregate comprising a ciliary marginal zone-like structure induced to differentiate from pluripotent stem cells" are cells obtained by dispersing:
a cell aggregate comprising a ciliary marginal zone-like structure induced to differentiate from pluripotent stem cells, or
a ciliary marginal zone-like structure separated from the cell aggregate (hereinafter sometimes referred to as the stem cell production method 3 of the present invention);

[4] the method according to the above-mentioned [1], wherein the step (1) is performed followed by performing the step (2), and wherein the "cells obtained from a cell aggregate comprising a ciliary marginal zone-like structure induced to differentiate from pluripotent stem cells" in step (1) are cells obtained by dispersing:
a cell aggregate comprising a ciliary marginal zone-like structure induced to differentiate from pluripotent stem cells, or
a ciliary marginal zone-like structure separated from the aforementioned cell aggregate; and the "cells obtained from a cell aggregate comprising a ciliary marginal zone-like structure induced to differentiate from pluripotent stem cells" in step (2) are cells obtained by dispersing the retinosphere obtained in the step (1) (hereinafter sometimes referred to as the stem cell production method 4 of the present invention);

[5] the method according to the above-mentioned [1], wherein the step (2) is performed followed by performing the step (1), and wherein the "cells obtained from a cell aggregate comprising a ciliary marginal zone-like structure induced to differentiate from pluripotent stem cells" in step (2) are cells obtained by dispersing:

a cell aggregate comprising a ciliary marginal zone-like structure induced to differentiate from pluripotent stem cells, or a ciliary marginal zone-like structure separated from the cell aggregate; and the "cells obtained from a cell aggregate comprising a ciliary marginal zone-like structure induced to differentiate from pluripotent stem cells" in step (1) are cells obtained by dispersing cells collected in the step (2) (hereinafter sometimes referred to as the stem cell production method 5 of the present invention);

[6] the method according to any one of the above-mentioned [1], [3], [4] and [5], wherein the SSEA-1 positive cell is further Rax positive;

[7] the method according to any one of the above-mentioned [1], [3], [4], [5], and [6], wherein the SSEA-1 positive cell is non-pigmented;

[8] the method according to any one of the above-mentioned [1], [2], [4] and [5], wherein the floating culturing in step (1) is performed in a serum-free medium or serum-containing medium each containing one or more substances selected from the group consisting of substances acting on the FGF signal transduction pathway and substances acting on the EGF signal transduction pathway;

[9] the method according to the above-mentioned [8], wherein the serum-free medium or serum-containing medium further comprises a ROCK inhibitor;

[10] the method according to any one of the above-mentioned [1], [2], [4], [5], [8] and [9], wherein the retinosphere is non-pigmented;

[11] the method according to any one of the above-mentioned [1] to [10], wherein the pluripotent stem cell is a primate pluripotent stem cell;

[12] the method according to any one of the above-mentioned [1] to [11], wherein the pluripotent stem cell is a human pluripotent stem cell;

[13] a method for producing a retinal layer-specific neuron, comprising a step of culturing a ciliary marginal zone stem cell obtained by the method of any one of the above-mentioned [1] to [12] in the presence of one or more substances selected from the group consisting of Notch signal inhibitory substances, retinoid and taurine;

[14] a therapeutic agent for a disease due to a disorder of a retinal tissue, comprising a ciliary marginal zone stem cell or retinal layer-specific neuron produced by the method of any one of the above-mentioned [1] to [13];

[15] a method of treating a disease due to a disorder of a retinal tissue, comprising transplanting an effective amount of a ciliary marginal zone stem cell or retinal layer-specific neuron produced by the method of any one of the above-mentioned [1] to [13] to a subject in need of the transplantation;

[16] a ciliary marginal zone stem cell or retinal layer-specific neuron produced by the method of any one of the above-mentioned [1] to [13] for use in the treatment of a disease due to a disorder of a retinal tissue;

[17] a reagent for evaluation of toxicity or drug efficacy, comprising a ciliary marginal zone stem cell or retinal layer-specific neuron produced by the method of any one of the above-mentioned [1] to [13];

[18] a method of evaluating toxicity or drug efficacy of a test substance, comprising bringing a ciliary marginal zone stem cell or retinal layer-specific neuron produced by the method of any one of the above-mentioned [1] to [13], into contact with the substance, and assaying an influence of the substance on the cell;

and so on.

Effect of the Invention

According to the present invention, a ciliary marginal zone stem cell having differentiation potency into a retinal cell including a retinal layer-specific neuron and self-replication ability can be produced efficiently with a high purity.

BRIEF DESCRIPTION OF THE DRAWINGS

FIG. 8 "B" shows FACS analysis results of Rax positive and SSEA-1 positive cell fraction separated from the above-mentioned cell suspension (Fraction 1 separated from the cell shown in "A" Q2), and FIG. 8 "C" shows FACS analysis results of Rax positive and SSEA-1 negative cell fraction separated from the aforementioned cell suspension (Fraction 2 separated from the cell shown in "A" Q4).

DESCRIPTION OF EMBODIMENTS

Figure 1:
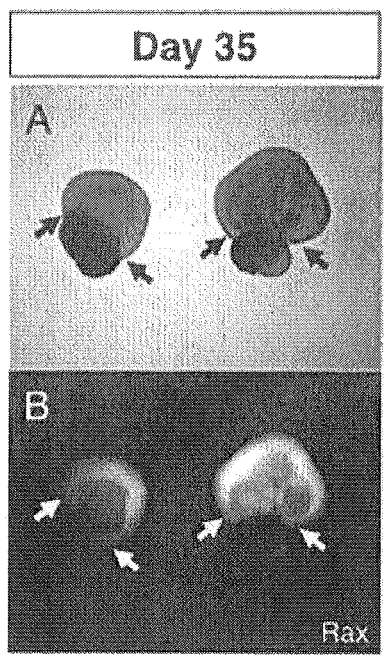
FIG. 1 shows a phase-contrast image (A) and a GFP fluorescence image (B) (Rax) of a cell aggregate comprising a ciliary marginal zone-like structure (day 35 from the start of floating culture).

The mode for carrying out the present invention is explained in detail below.

In the present invention, examples of the "stem cell" include a cell having an ability to differentiate into plural differentiation lineages (pluripotency), and an ability to grow in a sustained manner while maintaining multipotency (self-replication ability), which can regenerate a tissue when it is injured. Here, the "stem cell" may be an embryonic stem cell (ES cell) or a tissue stem cell (also called tissular stem cell, tissue-specific stem cell or somatic stem cell), or an artificial pluripotent stem cell (iPS cell: induced pluripotent stem cell) but is not limited thereto. As is appreciated from the fact that the stem cell-derived tissue cell can regenerate a tissue, it is known that the stem cell can differentiate into a normal cell close to one in a living body.

The "tissue stem cell" in the present invention is, for example, a cell present in a tissue which has an ability to differentiate into plural differentiation lineages constituting the tissue (pluripotency), and self-replication ability. The "tissue stem cells" are known to have a role of supplying new cells during developmental processes, cell death, and regeneration of damaged tissue.

Examples of the "pluripotent stem cell" in the present invention include a stem cell that can be cultured in vitro and has an ability to differentiate into any cell (triploblast (ectoderm, mesoderm, endoderm)-derived tissue) constituting a living body (pluripotency), including an embryonic stem cell (ES cell). The "pluripotent stem cell" is obtained from fertilized egg, clone embryo, reproductive stem cell, and tissue stem cell. It also includes a cell having induced pluripotent similar to that of embryonic stem cells, after introducing several kinds of genes into a somatic cell (also called artificial pluripotent stem cell). Pluripotent stem cell can be produced by a method known per se. Examples of the production method of the pluripotent stem cell include the methods described in Cell 131(5) pp. 861-872 (2007), Cell 126(4) pp. 663-676 (2006), etc.

Examples of the "embryonic stem cell (ES cell)" in the present invention include a stem cell having a self-replication ability and multipotency (particularly, "pluripotency"), which is a pluripotent stem cell derived from an early embryo. Embryonic stem cell was first established in 1981, and has also been applied to the generation of knockout mouse since 1989. In 1998, a human embryonic stem cell was established, which is also being utilized for regenerative medicine.

Examples of the "artificial pluripotent stem cell" in the present invention include a cell induced to have pluripotency by directly reprogramming a differentiated cell such as fibroblast etc. by the expression of several kinds of genes such as Oct3/4, Sox2, Klf4, and Myc, which was established by Yamanaka's group. in mouse cell in 2006 (Takahashi K and Yamanaka S. Cell. 2006, 126(4), p 663-676). In 2007, the artificial pluripotent stem cell was also established in human fibroblast, and has multipotency similar to that of embryonic stem cells (Cell, 131(5), pp. 861-872 (2007); Science, 318(5858), pp. 1917-1920 (2007); Nat Biotechnol., 26(1), pp. 101-106 (2008)).

Pluripotent stem cells are available from given organizations, or a commercially available product can be purchased. For example, human embryonic stem cells, KhES-1, KhES-2 and KhES-3, are available from Kyoto University's Institute for Frontier Medical Sciences. EB5 cell, which is a mouse embryonic stem cell, is available from Incorporated Administrative Agency RIKEN, and D3 cell line is available from ATCC, respectively.

Pluripotent stem cell can be maintained by culturing according to a method known per se. For example, human stem cell can be maintained by culturing using Knockout™ Serum Replacement (KSR). For example, mouse stem cell can be maintained by culturing with addition of fetal bovine serum (FBS) and a leukemia inhibitory factor (LIF), and without feeder cell.

Genetically-modified pluripotent stem cells can be produced by using, for example, a homologous recombination technique. Examples of the gene on the chromosome to be modified include a cell marker gene, a histocompatibility antigen gene, a gene related to a disease due to a disorder of nerve system cell and so on. A target gene on the chromosome can be modified using the methods described in Manipulating the Mouse Embryo, A Laboratory Manual, Second Edition, Cold Spring Harbor Laboratory Press (1994); Gene Targeting, A Practical Approach, IRL Press at Oxford University Press (1993); Biomanual Series 8, Gene Targeting, Making of Mutant Mouse using ES cell, YODOSHA CO., LTD. (1995); and so on.

To be specific, for example, the genomic gene of the target gene to be modified (e.g., cell marker gene, histocompatibility antigen gene, disease-related gene and so on) is isolated, and a targeting vector used for homologous recombination of the target gene is produced using the isolated genomic gene. The produced targeting vector is introduced into stem cells and the cells that showed homologous recombination between the target gene and the targeting vector are selected, whereby stem cells having the modified gene on the chromosome can be produced.

Examples of the method for isolating genomic gene of the target gene include known methods described in Molecular Cloning, A Laboratory Manual, Second Edition, Cold Spring Harbor Laboratory Press (1989), Current Protocols in Molecular Biology, John Wiley & Sons (1987-1997) and so on. The genomic gene of the target gene can also be isolated using genomic DNA library screening system (manufactured by Genome Systems), Universal GenomeWalker Kits (manufactured by CLONTECH) and so on.

Production of targeting vector used for homologous recombination of the target gene, and efficient selection of a homologous recombinant can be performed according to the methods described in Gene Targeting, A Practical Approach, IRL Press at Oxford University Press (1993); Biomanual Series 8, Gene Targeting, Making of Mutant Mouse using ES cell, YODOSHA CO., LTD. (1995); and so on. As the targeting vector, any of replacement type or insertion type can be used. As the selection method, methods such as positive selection, promoter selection, negative selection, polyA selection and so on can be used.

Examples of a method for selecting the object homologous recombinant from the selected cell lines include Southern hybridization method, PCR method and so on for the genomic DNA.

Examples of the "aggregate" in the present invention include a mass of the cells dispersed in the medium but gathered to form same. The "aggregate" in the present invention includes an aggregate formed by the cells dispersed at the start of the floating culture and an aggregate already formed at the start of the floating culture.

To "form aggregate" means to aggregate cells to form a cell aggregate. When an aggregate of stem cells is to be formed, dispersed stem cells may be aggregated naturally. Qualitatively uniform aggregate of stem cells may be formed by rapidly aggregating a given number of dispersed stem cells. For example, when pluripotent stem cells are rapidly gathered to allow formation of an aggregate of the pluripotent stem cells, an epithelium-like structure can be formed with good reproducibility in the cells induced to differentiate from the formed aggregate.

Examples of the experimental operation to form an aggregate include a method involving seeding cells in a floating culture dish having large wells and awaiting inartificial aggregation, a method involving keeping cells in a small space by using a plate with small wells (96 well plate), micropore and so on, a method involving aggregating cells by centrifugation for a short time using a small centrifugation tube, and so on.

Formation of aggregates of pluripotent stem cells and formation of an epithelium-like structure in each cell forming the aggregate can be determined based on the size and cell number of cell aggregates, macroscopic morphology, microscopic morphology by tissue staining analysis and uniformity thereof, expression of differentiation and undifferentiation markers and uniformity thereof, control of expression of differentiation marker and synchronism thereof, reproducibility of differentiation efficiency between aggregates, and so on.

Examples of the "tissue" in the present invention include a structure of a cell population, which has a conformation wherein more than one type of cell different in the shape and property are sterically configured in a given pattern.

In the present invention, examples of the "retinal tissue" include a retinal tissue etc. wherein at least two or more types of cells such as photoreceptor cell, rod cell, corn cell, horizontal cells, bipolar cells, amacrine cells, retinal ganglion cells (or ganglion cells), progenitor cells thereof, retinal progenitor cells and so on, which constitute respective retinal layers in in vivo retina, are sterically arranged in layers. With regard to each cell, which cell constitutes which retinal layer can be checked by a known method, for example, presence or absence of the expression of differentiation marker and undifferentiation marker or the level thereof, etc.

As the "retinal tissue" in the present invention, an epithelial tissue containing a retinal progenitor cell or neural retinal progenitor, which can be formed on a surface of a cell aggregate of pluripotent stem cells by floating culture of the aggregate under conditions suitable for differentiation into retina, can also be mentioned.

The "retinal layer" in the present invention means each layer constituting the retina. Specific examples thereof include retinal pigment epithelial layer, photoreceptor layer, external limiting membrane, outer nuclear layer, outer plexiform layer, inner nuclear layer, inner plexiform layer, ganglion cell layer, nerve fiber layer and inner limiting membrane.

The "retinal layer-specific neuron" in the present invention includes, for example, a cell constituting a retina layer which is a nerve cell specific to the retina layer. Specific Examples of the retinal layer-specific neuron include photoreceptor cell, rod cell, corn cell, horizontal cell, bipolar cell, amacrine cell, retinal ganglion cell (or ganglion cell), and pigment epithelium cell.

Examples of the "retinal stem cell" in the present invention include a cell having an ability to differentiate into any mature retina cells of photoreceptor cell, rod cell, corn cell, horizontal cell, bipolar cell, amacrine cell, retinal ganglion cell (or ganglion cell), and pigment epithelium cell, and self-replication ability.

As the "retinal progenitor cell" in the present invention, a progenitor cell capable of differentiating into any mature retina cell constituting the neural retina and the retinal pigment epithelium can be mentioned.

As the "neural retinal progenitor", a progenitor cell which is a cell destined to form an inner layer of the optic cup and capable of differentiating into any mature cell constituting the neural retina can be mentioned.

Examples of the retinal cell marker include Rax and PAX6 expressed in retinal progenitor cell, Chx10 expressed in neural retinal progenitor cell, Nkx2.1 expressed in progenitor cell of hypothalamus neuron but not expressed in retinal progenitor cell, Sox1 expressed in hypothalamus neuroepithelium but not expressed in retina, Crx expressed in progenitor cell of photoreceptor cell, and so on. Examples of the marker of the retinal layer-specific neuron include Chx10 and L7 expressed in bipolar cell, TUJI and Brn3 expressed in ganglion cell, Calretinin expressed in amacrine cell, Calbindin expressed in horizontal cell, Rhodopsin and Recoverin expressed in photoreceptor cell, RPE65 and Mitf expressed in pigment epithelium cell, Nrl expressed in rod cell, Rxr-gamma expressed in cone cell and so on.

Examples of the "ciliary marginal zone (CMZ)" in the present invention include a tissue present in the boundary region of retinal tissue (specifically, neural retina) and retinal pigment epithelium in the in vivo retina, which is a region including a tissue stem cell of retina (retinal stem cell). Ciliary marginal zone is also called a ciliary margin or retinal margin, and the ciliary marginal zone, ciliary margin and retinal margin are equivalent tissues. It is known that the ciliary marginal zone plays an important role in the supply of retinal progenitor cells and differentiated cells to retinal tissues, maintenance of retinal tissue structure and so on. Examples of the marker gene of the ciliary marginal zone include Rdh10 gene (positive), Otx1 gene (positive) and so on.

The "medium" to be used in the present invention can be prepared from a medium used for culture of animal cell as a basal medium. Examples of the basal medium include media that can be used for culturing animal cells such as BME medium, BGJb medium, CMRL1066 medium, Glasgow MEM medium, Improved MEM Zinc Option medium, IMDM medium, Medium199 medium, Eagle MEM medium, αMEM medium, DMEM medium, ham medium, F-12 medium, DMEM/F-12 medium, RPMI1640 medium, Fischer's medium, and mixed medium thereof etc.

Examples of the "serum-free medium" in the present invention include a medium free of unadjusted or unpurified serum. In the present invention, a medium containing purified blood-derived components and animal tissue-derived components (e.g., growth factor) is also included in a serum-free medium unless unadjusted or unpurified serum is contained therein.

The serum-free medium may contain a serum replacement. Examples of the serum replacement include albumin, transferrin, fatty acid, collagen precursor, trace element, 2-mercaptoethanol or 3' thiolglycerol, one appropriately containing equivalents of these etc., and soon. Such serum replacement may be prepared by, for example, the method described in WO98/30679 and so on. In addition, the serum replacement may be a commercially available product. Examples of such commercially available serum replacement include Knockout™ Serum Replacement (Invitrogen: hereinafter sometimes to be indicated as KSR), Chemically Defined Lipid Concentrate (manufactured by Gibco) and Glutamax (manufactured by Gibco).

The "serum-free medium" to be used for floating culture may contain fatty acid, lipid, amino acid (e.g., non-essential amino acid), vitamin, growth factor, cytokine, antioxidant, 2-mercaptoethanol, pyruvic acid, buffering agent, inorganic salts and so on.

To avoid complicated preparation, a serum-free medium (GMEM or DMEM medium, supplemented with 0.1 mM 2-mercaptoethanol, 0.1 mM non-essential amino acid Mix and 1 mM sodium pyruvate; or a 1:1 mixture of F-12 medium and IMDM medium supplemented with 450 μM 1-monothioglycerol etc.) supplemented with an appropriate amount (e.g., about 1-about 20%) of commercially available KSR can be preferably mentioned as the serum-free medium.

Examples of the "serum-containing medium" in the present invention include a medium containing unadjusted or unpurified serum. The medium may contain fatty acid, lipid, amino acid (e.g., non-essential amino acid), vitamin, growth factor, cytokine, antioxidant, 2-mercaptoethanol, pyruvic acid, buffering agent, inorganic salts and so on.

Examples of the "serum" to be added to the medium in the present invention include mammalian sera such as bovine serum, calf serum, fetal bovine serum, horse serum, colt serum, fetal horse serum, rabbit serum, leveret serum, fetal rabbit serum, and human serum, and so on.

In the present invention, the "medium containing substance X" is a medium supplemented with an exogenous substance X or a medium containing an exogenous substance X, and the "medium free of substance X" is a medium not supplemented with an exogenous substance X or a medium free of an exogenous substance X. As used herein, the "exogenous substance X" means substance X exogeneous to the cell or tissue cultured in the medium, and excludes endogenous substance X produced by the cell or tissue.

For example, the "medium containing a substance acting on the FGF signal transduction pathway" is a medium supplemented with an exogenous substance acting on the FGF signal transduction pathway or a medium containing an exogeneous substance acting on the FGF signal transduction pathway. The "medium free of a substance inhibiting FGF signal pathway" is a medium not supplemented with an exogeneous substance inhibiting FGF signal pathway or a medium free of an exogeneous substance inhibiting FGF signal pathway.

Examples of the "floating culture" in the present invention include culture of cell aggregates in a medium under non-adhesive conditions to a cell culture vessel, and so on.

The cell culture vessel to be used in floating culture is not particularly limited as long as it enables floating culture of the cells. Examples of such cell culture vessel include flask, tissue culture flask, dish, petri dish, tissue culture dish, multidish, microplate, microwell plate, micropore, multi-plate, multiwell plate, chamber slide, schale, tube, tray, culture bag, roller bottle and so on. A preferable vessel is a cell non-adhesive vessel.

As a cell non-adhesive vessel, one having its surface not artificially treated to improve cell adhesiveness (e.g., coating treatment with extracellular matrix, etc.) and so on may be used. As a cell non-adhesive vessel, a vessel having a surface artificially treated to lower adhesiveness to the cells (e.g., superhydrophobic treatment) etc. may be used.

The stem cell production method 1 of the present invention is a method for producing a ciliary marginal zone stem cell induced to differentiate from a pluripotent stem cell, comprising either the following step (1) or step (2), or both of these steps:
(1) a step of floating culturing cells obtained from a cell aggregate comprising a ciliary marginal zone-like structure induced to differentiate from pluripotent stem cells, thereby obtaining a retinosphere; and
(2) a step of collecting SSEA-1 positive cells from cells obtained from a cell aggregate comprising a ciliary marginal zone-like structure induced to differentiate from pluripotent stem cells.

"a ciliary marginal zone stem cell induced to differentiate from a pluripotent stem cell" in the present invention is present in a cell aggregate comprising a ciliary marginal zone-like structure induced to differentiate from pluripotent stem cells, and has differentiation potency into a retinal cell such as photoreceptor cell and self-replication ability. The above-mentioned ciliary marginal zone stem cell is SSEA-1 positive, and Rax gene positive, Chx10 gene positive, Rdh10 gene positive, Otx1 gene positive, Crx gene negative, and β3-tubulin (TuJ1) gene negative. The ciliary marginal zone stem cell is a non-pigmented cell. Such stem cell in a ciliary marginal zone is useful as a reagent for use for the evaluation of toxicity or drug efficacy of chemical substances and so on, or a material for use for the tests or treatments aiming at cell therapy and so on.

SSEA-1 (stage specific embryonic antigen-1) is an antigen expressed by a cell, and is also called CD15 or Lewis X (LeX). SSEA-1 is sometimes expressed on a cell surface.

The "SSEA-1 positive cell" in the present invention is a cell in which expression of SSEA-1 is detected.

Examples of the pluripotent stem cell include primate pluripotent stem cells, more specifically, human pluripotent stem cells. Examples of the pluripotent stem cell include embryonic stem cells and artificial pluripotent stem cells.

The "cell aggregate comprising a ciliary marginal zone-like structure induced to differentiate from pluripotent stem cells" to be used in step (1) and step (2) of the stem cell production method 1 of the present invention can be prepared, for example, by the following method:
a method for producing a cell aggregate comprising a ciliary marginal zone-like structure, which includes a step of culturing a cell aggregate comprising a retinal tissue in which Chx10 positive cells are present in a proportion of 20% or more and 100% or less of the tissue in a serum-free medium or serum-containing medium each containing a substance acting on the Wnt signal pathway and a substance inhibiting the FGF signal pathway for only a period before the appearance of a RPE65 gene-expressing cell, followed by culturing the resulting "cell aggregate in which a RPE65 gene-expressing cell does not appear" in a serum-free medium or serum-containing medium each free of a substance acting on the Wnt signal pathway (hereinafter sometimes referred to as the present cell aggregate production method 1).

The "cell aggregate comprising a retinal tissue" to be used as a starting material in the present cell aggregate production method 1 is a cell aggregate in which Chx10 positive cells are present in the retinal tissue in a proportion of 20% or more and 100% or less of the tissue. The aforementioned "proportion of Chx10 positive cells" is, for example, preferably 40% or more, more preferably 60% or more.

The above-mentioned "cell aggregate comprising a retinal tissue" can be prepared, for example, from a pluripotent stem cell, preferably human pluripotent stem cell.

As a method for preparing the above-mentioned "cell aggregate comprising a retinal tissue", for example, a method including the following steps (A) and (B) can be mentioned:
(A) a step of subjecting pluripotent stem cells to floating culture in a serum-free medium to form an aggregate of pluripotent stem cells, and
(B) a step of performing floating culture of the aggregate formed in step (A) in a serum-free medium or serum-containing medium each free of a substance acting on the Sonic hedgehog signal transduction pathway and containing a substance acting on the BMP signal transduction pathway to give a cell aggregate comprising a retinal progenitor cell.

The step (A) forming an aggregate of pluripotent stem cells by floating culture of pluripotent stem cells in a serum-free medium is explained.

The serum-free medium used in step (A) is not particularly limited as long as it is as mentioned above. For example, a serum-free medium supplemented with an appropriate amount of a commercially available serum replacement such as KSR and so on (e.g., medium of 1:1 mixture of IMDM and F-12 supplemented with 10% KSR, 450 μM 1-monothioglycerol and 1× Chemically Defined Lipid Concentrate) can be mentioned. The amount of KSR to be added to a serum-free medium in the case of human ES cells is generally about 1% to about 20%, preferably about 2% to about 20%.

The culture conditions such as culture temperature, $CO_2$ concentration and so on in step (A) can be appropriately determined. The culture temperature is, for example, about 30° C. to about 40° C., preferably about 37° C. The $CO_2$ concentration is, for example, about 1% to about 10%, preferably about 5%.

The concentration of the pluripotent stem cells in step (A) can be determined as appropriate to form aggregates of pluripotent stem cells more uniformly and efficiently. For example, when human ES cells are subjected to floating culture using a 96 well microwell plate, a liquid prepared to about $1\times10^3$ to about $1\times10^5$ cells, preferably about $3\times10^3$ to about $5\times10^4$ cells, more preferably about $5\times10^3$ to about $3\times10^4$ cells, most preferably about $1.2\times10^4$ cells, per well is added to the well, and the plate is left standing to form cell aggregates.

The time of floating culture necessary forming cell aggregates can be determined as appropriate according to the pluripotent stem cell to be used, so that the cells can be aggregated uniformly. To form uniform cell aggregates, it is desirably as short as possible. For example, in the case of human ES cells, aggregates are formed preferably within about for 24 hr, more preferably within about for 12 hr. The time for cell aggregate formation can be appropriately adjusted by controlling the tools for aggregating the cells, centrifugation conditions and so on.

The step (B) for obtaining a cell aggregate comprising a retinal progenitor cell by floating culture of the cell aggregate formed in step (A) in a serum-free medium or serum-containing medium each free of a substance acting on the Sonic hedgehog signal transduction pathway and containing a substance acting on the BMP signal transduction pathway is explained.

The medium to be used in step (B) is a serum-free medium or serum-containing medium not supplemented with a substance acting on the Sonic hedgehog signal transduction pathway and supplemented with a substance acting on the BMP signal transduction pathway, which does not require addition of a basement membrane preparation.

A serum-free medium or serum-containing medium to be used for such medium is not particularly limited as long as it is as mentioned above. For example, a serum-free medium supplemented with an appropriate amount of a commercially available serum replacement such as KSR and so on (e.g., medium of 1:1 mixture of IMDM and F-12 supplemented with 10% KSR, 450 µM 1-monothioglycerol and 1× Chemically Defined Lipid Concentrate) can be mentioned. The amount of KSR to be added to a serum-free medium in the case of human ES cells is generally about 1% to about 20%, preferably about 2% to about 20%.

As the serum-free medium to be used in step (B), the serum-free medium used in step (A) may be directly used, or may be replaced with a fresh serum-free medium. When the serum-free medium used in step (A) is directly used for step (B), a substance acting on the BMP signal transduction pathway may be added to the medium.

The substance acting on the Sonic hedgehog (hereinafter sometimes to be indicated as Shh) signal transduction pathway is a substance capable of enhancing signal transduction mediated by Shh. Examples of the substance acting on the Shh signal transduction pathway include protein belonging to the Hedgehog family (e.g., Shh), Shh receptor, Shh receptor agonist, Purmorphamine, or SAG and so on.

The substance acting on the BMP signal transduction pathway is a substance capable of enhancing signal transduction mediated by BMP. Examples of the substance acting on the BMP signal transduction pathway include BMP proteins such as BMP2, BMP4, BMP7 etc., GDF proteins such as GDF7 etc., anti-BMP receptor antibody, BMP partial peptide and so on. BMP2 protein, BMP4 protein and BMP7 protein are available from, for example, R&D Systems, and GDF7 protein is available from, for example, Wako Pure Chemical Industries, Ltd.

The concentration of a substance acting on the BMP signal transduction pathway only needs to be a concentration at which differentiation of the cells, that form an aggregate of pluripotent stem cells, into retinal cells can be induced. For example, in the case of BMP4, it is added to the medium to a concentration of about 0.01 nM to about 1 µM, preferably about 0.1 nM to about 100 nM, more preferably about 1.5 nM.

A substance acting on the BMP signal transduction pathway only needs to be added after about for 24 hr from the start of the floating culture in step (A), and may be added to a medium within several days (e.g., within 15 days) from the start of the floating culture. Preferably, a substance acting on the BMP signal transduction pathway is added to a medium between day 1 and day 15, more preferably between day 1 and day 9, further preferably day 6, from the start of the floating culture.

After addition of a substance acting on the BMP signal transduction pathway to the medium, and after the start of the differentiation induction of the cells forming an aggregate of pluripotent stem cells into retinal cells, addition of the substance acting on the BMP signal transduction pathway to the medium is not necessary, and the medium may be exchanged with a serum-free medium or serum-containing medium each free of a substance acting on the BMP signal transduction pathway. In this way, the cost of medium can be suppressed. The cells that started differentiation induction into retinal cells can be checked by, for example, detecting the expression of Rax gene in the cells. The cell aggregate formed in step (A) by using pluripotent stem cells knocked-in with a fluorescence reporter protein gene such as GFP and so on into the Rax gene locus is subjected to floating culture in the presence of a substance acting on the BMP signal transduction pathway at a concentration necessary for differentiation induction into retinal cell, and fluorescence emitted from the expressed fluorescence reporter protein is detected, whereby the time period when differentiation induction into retinal cell was started can be checked. One embodiment of step (B) is a step for obtaining a cell aggregate comprising retinal progenitor cell, by floating culture of the cell aggregate formed in step (A) in a serum-free medium or serum-containing medium each free of a substance acting on the Sonic hedgehog signal transduction pathway but containing a substance acting on the BMP signal transduction pathway at a concentration necessary for differentiation induction into retinal cell, until a cell expressing Rax gene starts to appear.

The culture conditions such as culture temperature, $CO_2$ concentration and so on in step (B) can be appropriately determined. The culture temperature is, for example, about 30° C. to about 40° C., preferably about 37° C. The $CO_2$ concentration is, for example, about 1% to about 10%, preferably about 5%.

That a cell aggregate comprising a retinal progenitor cell was obtained can be checked by, for example, detecting the presence of a cell expressing Rax or PAX6, which is a retinal progenitor cell marker, in the aggregate. The "cell aggregate comprising a retinal progenitor cell" obtained by the method including above-mentioned steps (A) and (B) can be used as a "cell aggregate comprising a retinal tissue" as a starting material in the present cell aggregate production method 1.

The "cell aggregate comprising a retinal tissue" to be used as a starting material in the present cell aggregate production method 1 can also be specifically prepared, for example, by a method including the following steps (C), (D) and (E):

(C) a step of subjecting pluripotent stem cells to floating culture in a serum-free medium containing a substance inhibiting the Wnt signal pathway to form an aggregate of pluripotent stem cells, (D) a step of subjecting the cell aggregate formed in step (C) to floating culture in a serum-free medium containing a basement membrane preparation, and (E) a step of subjecting the cell aggregate cultured in step (D) to floating culture in a serum-containing medium.

A substance inhibiting the Wnt signal pathway to be used in step (C) is not particularly limited as long as it can suppress signal transduction mediated by Wnt. Examples of the substance inhibiting the Wnt signal pathway include Dkk1, Cerberus protein, Wnt receptor inhibitor, soluble-type Wnt receptor, Wnt antibody, casein kinase inhibitor, dominant negative Wnt protein, CKI-7 (N-(2-aminoethyl)-5-chloro-isoquinoline-8-sulfonamide), D4476 (4-{4-(2,3-dihydrobenzo[1,4]dioxin-6-yl)-5-pyridin-2-yl-1H-imidazol-2-yl}benzamide), IWR-1-endo (IWR1e), IWP-2 and so on. The concentration of the substance inhibiting the Wnt signal pathway only needs to be a concentration at which aggregates of pluripotent stem cells are formed. For example, a common substance inhibiting the Wnt signal pathway such as IWR1e is added at a concentration of about 0.1 μM to about 100 μM, preferably about 1 μM to about 10 μM, more preferably around 3 μM.

A substance inhibiting the Wnt signal pathway may be added to serum-free medium before the start of the floating culture, or added to a serum-free medium within several days from the start of the floating culture (e.g., within 5 days). Preferably, a substance inhibiting the Wnt signal pathway is added to a serum-free medium within 5 days, more preferably within 3 days, from the start of the floating culture, most preferably simultaneously with the start of the floating culture. In addition, floating culture is performed up to day 18, more preferably day 12, from the start of the floating culture with the addition of a substance inhibiting the Wnt signal pathway.

The culture conditions such as culture temperature and $CO_2$ concentration in step (C) can be appropriately determined. While the culture temperature is not particularly limited, it is, for example, about 30° C. to about 40° C., preferably around about 37° C. The $CO_2$ concentration is, for example, about 1% to about 10%, preferably around about 5%.

The concentration of the pluripotent stem cells in step (C) can be determined as appropriate by those of ordinary skill in the art to form aggregates of pluripotent stem cells more uniformly and efficiently. The concentration of the pluripotent stem cells when forming cell aggregates is not particularly limited as long as it permits formation of uniform aggregates of stem cells. For example, when human ES cells are subjected to floating culture using a 96 well microwell plate, a liquid prepared to about $1 \times 10^3$ to about $5 \times 10^4$ cells, preferably about $3 \times 10^3$ cells to about $3 \times 10^4$ cells, more preferably about $5 \times 10^3$ cells to about $2 \times 10^4$ cells, most preferably around $9 \times 10^3$ cells, per well is added, and the plate is left standing to form cell aggregates.

The time of floating culture necessary forming cell aggregates can be determined as appropriate according to the pluripotent stem cell to be used, as long as the cells can be aggregated rapidly. To form uniform cell aggregates, it is desirably as short as possible. For example, in the case of human ES cells, cell aggregates are desirably formed preferably within for 24 hr, more preferably within for 12 hr. The time for cell aggregate formation can be appropriately adjusted by those of ordinary skill in the art by controlling the tools for aggregating the cells, centrifugation conditions and so on.

The basement membrane preparation to be used in step (D) refers to one containing basement membrane-constituting components having a function to control cell morphology, differentiation, growth, motility, expression of function and so on which are similar to those of epithelial cell, when intended cells capable of forming a basement membrane are plated thereon and cultured. Here, the "basement membrane constituting component" refers to an extracellular matrix molecule in the morphology of a thin membrane present between epithelial cell layer and interstitial cell layer and so on in animal tissues. A basement membrane preparation can be produced by, for example, removing cells capable of forming a basement membrane, which adhere onto a support via a basement membrane, with a solution capable of dissolving the lipid of the cells, an alkali solution and so on. Examples of preferable basement membrane preparation include products commercially available as basement membrane components (e.g., Matrigel™ (manufactured by Becton, Dickinson and Company: hereinafter, sometimes referred to as Matrigel)), and extracellular matrix molecules known as basement membrane components (e.g., laminin, type IV collagen, heparan sulfate proteoglycan, entactin and so on).

Matrigel™ is a product prepared from a basement membrane derived from Engelbreth Holm Swarn (EHS) mouse sarcoma. The main component of Matrigel™ is type IV collagen, laminin, heparan sulfate proteoglycan, and entactin. In addition to these, TGF-β, fibroblast growth factor (FGF), tissue plasminogen activator, and a growth factor naturally produced by EHS tumor are contained. The "growth factor reduced (GFR) product" of Matrigel™ has a lower growth factor concentration than common Matrigel™. In the present invention, GFR product is preferably used.

While the concentration of the basement membrane preparation to be added to a serum-free medium for the floating culture in step (D) is not particularly limited as long as the epithelial structure of the neural tissue (e.g., retinal tissue) is stably maintained, for example, it is preferably 1/20 to 1/200 volume, more preferably around 1/100 volume, of the culture medium when Matrigel™ is used. While basement membrane preparation may already have been added to the medium when the culture of stem cell is started, it is preferably added to the serum-free medium within 5 days, more preferably within 2 days, from the start of the floating culture.

As the serum-free medium to be used in step (D), the serum-free medium used in the step (C) may be directly used, or may be replaced with a fresh serum-free medium.

When the serum-free medium used in the step (C) is directly used for step (D), the "basement membrane preparation" can be added to the medium.

The culture conditions such as culture temperature, and $CO_2$ concentration in step (D) can be appropriately determined. While the culture temperature is not particularly limited, it is, for example, about 30° C. to about 40° C., preferably around about 37° C. The $CO_2$ concentration is, for example, about 1% to about 10%, preferably around about 5%.

As the serum-containing medium to be used in step (E), may be used the serum-free medium used in the culture of step (D) to which a serum is directly added, or one replaced with a fresh serum-containing medium.

The serum is added on or after day 7, more preferably on or after day 9, most preferably on day 12, from the start of the floating culture. The concentration of the serum to be added is about 1% to about 30%, preferably about 3% to about 20%, more preferably around 10%.

In step (E), the production efficiency of retinal tissue can be increased by adding a substance acting on the Shh signal pathway in addition to the serum.

The substance acting on the Shh signal pathway is not particularly limited as long as it can enhance signal transduction mediated by Shh. Examples of the substance acting on the Shh signal pathway include proteins belonging to the Hedgehog family (e.g., Shh), Shh receptor, Shh receptor agonist, Purmorphamine, SAG andso on.

The concentration of the substance acting on the Shh signal pathway used in step (E) is, for example, in the case of common substance acting on the Shh signal pathway such as SAG, about 0.1 nM to about 10 µM, preferably about 10 nM to about 1 µM, more preferably around 100 nM.

In the thus-cultured cell aggregates, the retinal tissue is present to cover the surface of the cell aggregate. The retinal tissue can be checked by immunostaining method and so on. The cell aggregate obtained by the above-mentioned method including steps (C), (D) and (E) can be used as a "cell aggregate comprising a retinal tissue" to be a starting material in the present cell aggregate production method 1.

The presence of a retinal tissue in the cell aggregate obtained by the above-mentioned method including steps (A) and (B) or the above-mentioned method including steps (C), (D) and (E) can also be checked as follows. For example, the cell aggregates obtained by the above-mentioned method are subjected to floating culture in a serum-containing medium. Examples of the cell culture vessel to be used for floating culture include those mentioned above. Other culture conditions such as culture temperature, $CO_2$ concentration, and $O_2$ concentration of the floating culture can be appropriately determined. While the culture temperature is not particularly limited, it is, for example, about 30° C. to about 40° C. The $CO_2$ concentration is, for example, about 1% to about 10%. The $O_2$ concentration is, for example, about 20% to about 70%. While the culture period is not particularly limited, it is generally for 48 hr or more, preferably 7 days or more.

After completion of the floating culture, the cell aggregates are fixed with a fixative such as paraformaldehyde solution, and a cryosection is prepared. The obtained cryosection is immunostained, and the presence of retinal cells of each differentiation lineage (photoreceptor, horizontal cell, bipolar cell, amacrine cell, retinal ganglion cell etc.) is checked. The obtained cryosection is immunostained, and formation of a layer structure of retinal tissue may be checked. Since respective layers of a retinal tissue are composed of different retinal progenitor cells (photoreceptor, horizontal cell, bipolar cell, amacrine cell, retinal ganglion cell), formation of a layer structure can be checked by immunostaining using antibodies against the aforementioned markers expressed in these cells.

The "proportion of Chx10 positive cells" in a retinal tissue contained in the cell aggregate prepared as mentioned above can be examined by, for example, the following method.

(1) First, a cryosection of "a cell aggregate comprising a retinal tissue" is prepared.
(2) Then, immunostaining of Rax protein is performed. When a gene recombinant cell obtained by altering a Rax gene-expressing cell to express a fluorescence protein such as GFP is used, the expression of the aforementioned fluorescence protein, is observed using a fluorescence microscope and so on. A retinal tissue region expressing Rax gene is specified in the obtained immunostained images or fluorescence microscopic images.
(3) Using the same section as the cryosection wherein the retinal tissue region expressing Rax gene has been specified or an adjacent section as a sample, the nucleus is stained with a nuclear staining reagent such as DAPI. Then, the number of stained nuclei in the above-specified retinal tissue region expressing Rax gene is counted, whereby the number of the cells in the retinal tissue region is measured.
(4) Using the same section as the cryosection wherein the retinal tissue region expressing Rax gene has been specified or an adjacent section as a sample, Chx10 protein is immunostained. The number of Chx10 positive cells in the above-specified retinal tissue region is counted.
(5) Based on each number of nuclei measured in the above-mentioned (3) and (4), the number of nuclei in Chx10 positive cells is divided by the number of nuclei in the above-specified retinal tissue region expressing the Rax gene, whereby the "proportion of Chx10 positive cells" is calculated.

In the present cell aggregate production method 1, firstly, a cell aggregate comprising a retinal tissue in which Chx10 positive cells are present in a proportion of 20% or more and 100% or less of the tissue is cultured in a serum-free medium or serum-containing medium each containing a substance acting on the Wnt signal pathway and a substance inhibiting the FGF signal pathway for only a period before the appearance of a RPE65 gene-expressing cell.

As a preferable culture here, floating culture can be mentioned.

As a serum-free medium, a serum-free medium which is a basal medium supplemented with N2 or KSR can be mentioned. More specifically, a serum-free medium which is a DMEM/F-12 medium supplemented with N2 supplement (N2, Invitrogen) can be mentioned. As the serum-containing medium, a serum-containing medium which is a basal medium supplemented with fetal bovine serum can be mentioned.

The culture conditions such as culture temperature, $CO_2$ concentration can be appropriately set. The culture temperature is, for example, in the range of about 30° C. to about 40° C., preferably, for example, around about 37° C. The $CO_2$ concentration is, for example, in the range of about 1% to about 10%, preferably, for example, around about 5%.

The substance acting on the Wnt signal pathway to be contained in a serum-free medium or serum-containing medium when the above-mentioned "cell aggregate comprising a retinal tissue" is cultured in the medium is not particularly limited as long as it can enhance signal transduction mediated by Wnt. Specific examples of the substance acting on the Wnt signal pathway include protein belonging to Wnt family (e.g., Wnt1, Wnt3a, Wnt7a), Wnt receptor, Wnt receptor agonist, GSK3β inhibitor (e.g., 6-Bromoindirubin-3'-oxime (BIO), CHIR99021, Kenpaullone) and so on.

The concentration of the substance acting on the Wnt signal pathway to be contained in a serum-free medium or serum-containing medium in the case of a common substance acting on the Wnt signal pathway such as CHIR99021 is, for example, in the range of about 0.1 µM to about 100 µM, preferably, for example, in the range of about 1 µM to about 30 µM, more preferably, for example, around 3 µM.

The substance inhibiting the FGF signal pathway to be contained in a serum-free medium or serum-containing medium when the above-mentioned "cell aggregate comprising a retinal tissue" is cultured in the medium is not particularly limited as long as it can inhibit signal transduction mediated by FGF. Examples of the substance inhibiting FGF signal pathway include FGF receptor, FGF receptor inhibitor (e.g., SU-5402, AZD4547, BGJ398), MAP kinase cascade inhibitory substance (e.g., MEK inhibitor, MAPK inhibitor, ERK inhibitor), PI3 kinase inhibitor, Akt inhibitor and so on.

The concentration of a substance inhibiting FGF signal pathway contained in a serum-free medium or serum-containing medium only needs to be a concentration at which differentiation of the cells, that form an aggregate of pluripotent stem cells, into retinal cells can be induced. For example, in the case of SU-5402, it is added to the medium to a concentration of about 0.1 μM to about 100 μM, preferably about 1 μM to about 30 μM, more preferably about 5 μM.

"Culturing for only a period before the appearance of a RPE65 gene-expressing cell" in the present cell aggregate production method 1 means culturing in the whole or a part of the period before the appearance of a RPE65 gene-expressing cell. That is, culturing in the whole or a part of the period (any period) during which the "cell aggregate comprising a retinal tissue" in the culture system is constituted by cells that do not substantially express RPE65 gene suffices. By employing such culturing, a cell aggregate in which a RPE65 gene-expressing cell does not appear can be obtained. The "cell aggregate in which a RPE65 gene-expressing cell does not appear" includes a "cell aggregate in which a RPE65 gene-expressing cell does not appear at all" and "cell aggregate in which a RPE65 gene-expressing cell does not appear substantially". As the "cell aggregate in which a RPE65 gene-expressing cell does not appear substantially", a cell aggregate containing RPE65 positive cells at a ratio of about 1% or less in the retinal tissue contained in the cell aggregate can be mentioned.

To determine such particular period, the "cell aggregate comprising a retinal tissue" is used as a sample, and the presence or absence of expression of RPE65 gene contained in the sample only needs to be measured by a general genetic engineering method or a biochemical method. Specifically, for example, the presence or absence of expression of RPE65 gene or the level thereof can be examined by subjecting a cryosection of the aforementioned "cell aggregate comprising a retinal tissue" to an immunostaining method using an antibody against RPE65 protein.

A "period before the appearance of a RPE65 gene-expressing cell" is, for example, a period during which the ratio of Chx10 positive cells present in the above-mentioned retinal tissue decreases than that at the time of start of the culture of the aforementioned cell aggregate in a serum-free medium or serum-containing medium each containing a substance acting on the Wnt signal pathway and a substance inhibiting FGF signal pathway, and falls within the range of 30% to 0%. The "cell aggregate in which a RPE65 gene-expressing cell does not appear" is a cell aggregate in which Chx10 positive cells are present in the above-mentioned retinal tissue in a proportion of within 30% to 0% of the tissue.

While the number of days of the "period before the appearance of a RPE65 gene-expressing cell" varies depending on the kind of the substance acting on the Wnt signal pathway and the substance inhibiting the FGF signal pathway, the kind of the serum-free medium or serum-containing medium, other culture conditions and so on, it is, for example, within 14 days. More specifically, when a serum-free medium (e.g., serum-free medium which is a basal medium supplemented with N2) is used, the above-mentioned period is preferably, for example, within 10 days, more preferably, for example, 3 days to 6 days. When a serum-containing medium (e.g., serum-containing medium which is a basal medium supplemented with fetal bovine serum) is used, the aforementioned period is preferably, for example, within 12 days, more preferably, for example, 6 days to 9 days.

Then the "cell aggregate in which a RPE65 gene-expressing cell does not appear" obtained by culturing as mentioned above is cultured in a serum-free medium or serum-containing medium each free a substance acting on the Wnt signal pathway.

As a preferable culture here, floating culture can be mentioned.

As the serum-free medium, a medium which is a basal medium supplemented with N2 or KSR can be mentioned. As the serum-containing medium, a medium which is a basal medium supplemented with fetal bovine serum can be mentioned. More specifically, a serum-containing medium which is a DMEM/F-12 medium supplemented with fetal bovine serum can be mentioned.

The aforementioned serum-free medium or serum-containing medium may contain a known growth factor, an additive and a chemical substance that promote the growth, and so on. Examples of the known growth factor include EGF, FGF, IGF, insulin and so on. Examples of the additive that promotes the growth include N2 supplement (N2, Invitrogen), B27 supplement (Invitrogen), KSR and so on. Examples of the chemical substance that promotes the growth include retinoids (e.g., retinoic acid) and taurine.

A preferable culture period is, for example, a culture period during which the ratio of Chx10 positive cells present in the above-mentioned retinal tissue increases than that at the time of start of the culture of the aforementioned cell aggregate in a serum-free medium or serum-containing medium each free a substance acting on the Wnt signal pathway, and reaches 30% or more.

The culture conditions such as culture temperature, $CO_2$ concentration can be appropriately set. The culture temperature is, for example, in the range of about 30° C. to about 40° C., preferably, for example, around about 37° C. The $CO_2$ concentration is, for example, in the range of about 1% to about 10%, preferably, for example, around about 5%.

While the number of the above-mentioned culture days until "a cell aggregate comprising a ciliary marginal zone-like structure" is obtained varies depending on the kind of the serum-free medium or serum-containing medium, other culture conditions and so on, it is, for example, within 100 days. The aforementioned number of culture days is preferably, for example, 20 days to 70 days, more preferably, for example, 30 days to 60 days.

In the "cell aggregate comprising a ciliary marginal zone-like structure" produced as mentioned above, a retinal pigment epithelium and a retinal tissue (specifically, neural retina) are present adjacent to the ciliary marginal zone-like structure in the same cell aggregate. The structure can be checked by microscopic observation and so on. Specifically, for example, when a cell aggregate is produced from pluripotent stem cells wherein GFP gene is knocked into Rax gene locus (RAX::GFP knock-in cell), the presence of neural retina which is RAX::GFP strong positive region, retinal pigment epithelium which is an epithelial tissue in which pigmentation can be observed with transmitted light and, a ciliary marginal zone-like structure in a boundary region between neural retina and retinal pigment epithelium and having a characteristic structure can be checked by using a fluorescence stereoscopic microscope (e.g., SZX16 manufactured by Olympus Corporation).

In the "cell aggregate comprising a ciliary marginal zone-like structure" produced as mentioned above, a ciliary marginal zone-like structure is formed in a region between two neural retinal tissues. That is, a tissue continuously containing a neural retinal tissue, a ciliary marginal zone-like structure and another neural retinal tissue is sometimes formed. In this case, the presence of a ciliary marginal zone-like structure can be checked by microscopic observation since the ciliary marginal zone-like structure is characteristically thinner than the adjacent neural retinal tissue.

The "cell aggregate comprising a ciliary marginal zone-like structure, which was induced to differentiate from pluripotent stem cells" to be used in step (1) and step (2) of the stem cell production method 1 of the present invention can also be prepared, for example, by the following method described in patent document 1 (hereinafter sometimes referred to as the present cell aggregate production method 2): a method for producing a cell aggregate comprising a ciliary marginal zone-like structure, comprising a step of culturing a cell aggregate comprising a retinal tissue in which Chx10 positive cells are present in a proportion of 20% or more of the tissue in a serum-free medium or serum-containing medium each containing a substance acting on the Wnt signal pathway for only a period before the appearance of a RPE65 gene-expressing cell, followed by culturing the resulting "cell aggregate in which a RPE65 gene-expressing cell does not appear" in a serum-free medium or serum-containing medium each free of a substance acting on the Wnt signal pathway.

The "cell aggregate comprising a retinal tissue" to be used as a starting material in the present cell aggregate production method 2 is a cell aggregate in which Chx10 positive cells are present in the retinal tissue in a proportion of 20% or more of the tissue. The aforementioned "proportion of Chx10 positive cells" is, for example, preferably 40% or more, more preferably 60% or more. As a preparation method of such "cell aggregate comprising a retinal tissue", a method including steps (A) and (B), or a method including steps (C), (D) and (E), mentioned above as a preparation method of the starting material of the present cell aggregate production method 1, can be mentioned.

In step (1) of the stem cell production method 1 of the present invention, cells obtained from "a cell aggregate comprising a ciliary marginal zone-like structure induced to differentiate from pluripotent stem cells" prepared as mentioned above are subjected to floating culturing and a retinosphere is obtained.

Examples of the cells obtained from "a cell aggregate comprising a ciliary marginal zone-like structure induced to differentiate from pluripotent stem cells" include cells obtained by dispersing the above-mentioned "cell aggregate comprising a ciliary marginal zone-like structure induced to differentiate from pluripotent stem cells", cells obtained by dispersing a ciliary marginal zone-like structure separated from the aforementioned cell aggregate and cells obtained by dispersing cells collected from the aforementioned cell aggregate. When such cells are subjected to floating culture at a low density in the presence of a growth factor and the like, a spherical cell aggregate derived from one cell or a small number of cells such as 2 to about 10 cells, i.e., retinosphere, can be formed.

Examples of the method of separating a ciliary marginal zone-like structure from "a cell aggregate comprising a ciliary marginal zone-like structure induced to differentiate from pluripotent stem cells" include a method of dissecting with fine tweezers, scalpel etc. under a microscope. The presence of a ciliary marginal zone-like structure in "a cell aggregate comprising a ciliary marginal zone-like structure induced to differentiate from pluripotent stem cells" can be checked, for example, by the aforementioned method. Using a ciliary marginal zone-like structure cut out from "a cell aggregate comprising a ciliary marginal zone-like structure induced to differentiate from pluripotent stem cells", the content of the ciliary marginal zone stem cell in the cells at the time of start of the floating culture can be increased.

As a method for collecting cells from "a cell aggregate comprising a ciliary marginal zone-like structure induced to differentiate from pluripotent stem cells", a method for collecting SSEA-1 positive cell, which is performed in step (2) to be mentioned below, can be mentioned.

Examples of the method of dispersing a cell aggregate, a ciliary marginal zone-like structure or cells include mechanical dispersion treatment, cell dispersion treatment, and cell protector addition treatment. These treatments may be performed in combination. Preferably, a cell dispersion treatment is performed and then a mechanical dispersion treatment is performed.

As a method of mechanical dispersion treatment, a pipetting treatment can be mentioned.

As a cell dispersion to be used for the cell dispersion treatment, a solution containing enzymes such as trypsin, collagenase, hyaluronidase, elastase, pronase, papain and so on, and a chelating agent such as ethylenediaminetetraacetic acid and so on can be mentioned. Preferably, trypsin, papain or collagenase, more preferably, papain is used. A commercially available cell dispersion containing papain can also be used.

As a cell protector used for the cell protector addition treatment, a substance acting on the FGF signal transduction pathway, a substance acting on the EGF signal transduction pathway, heparin, a substance inhibiting the ROCK pathway, serum, and serum replacement can be mentioned.

For example, a cell aggregate, a ciliary marginal zone-like structure or cells are treated with a cell dispersion containing papain, and further dispersed by pipetting.

As a medium used for floating culture of the cells dispersed as mentioned above, a serum-free medium or serum-containing medium each supplemented with additives for nerve cell culture and a growth factor can be mentioned. Preferably, a serum-free medium or serum-containing medium each supplemented with one or more substance selected from the group consisting of a substance acting on the FGF signal transduction pathway and a substance acting on the EGF signal transduction pathway can be mentioned.

When a substance inhibiting the ROCK pathway is added to the above-mentioned medium, the retinosphere formation efficiency can be enhanced.

Heparin may also be added to the above-mentioned medium. Heparin is known to increase the effects of a substance acting on the FGF signal transduction pathway and a substance acting on the EGF signal transduction pathway.

Examples of the substance acting on the FGF signal transduction pathway to be used for the above-mentioned floating culture include FGF1, FGF2, FGF4, and FGF10. The concentration of FGF2 (bFGF) used as a substance acting on the FGF signal transduction pathway is, for example, about 1 ng/ml to about 200 ng/ml, preferably about 5 ng/ml to about 100 ng/ml, more preferably about 10 ng/ml to about 50 ng/ml.

Examples of the substance acting on the EGF signal transduction pathway include EGF, TGF-alpha, and HB-EGF. The concentration of EGF used as a substance acting on the EGF signal transduction pathway is, for example, about 1 ng/ml to about 100 ng/ml, preferably about 5 ng/ml to about 50 ng/ml, more preferably about 10 ng/ml to about 40 ng/ml.

The substance inhibiting the ROCK pathway is a substance capable of inhibiting signals mediated by Rho kinase. Examples of the substance inhibiting the ROCK pathway include Y-27632 and Fasudil. The concentration of Y-27632 to be added as a substance inhibiting the ROCK pathway is, for example, about 0.01 µM to about 100 µM, preferably about 1 µM to about 30 µM, more preferably about 10 µM.

The number of plated cells in the floating culture in step (1) is, for example, about $1\times10^2$ cells/ml to about $1\times10^6$ cells/ml, preferably about $1\times10^3$ cells/ml to about $5\times10^5$ cells/ml, more preferably about $5\times10^3$ cells/ml to about $1\times10^5$ cells/ml.

A culture material to be used for the above-mentioned floating culture is preferably a flat-bottomed low adhesive culture material.

The thus-formed retinosphere contains a self-replicated ciliary marginal zone stem cell. When the cell at the time of start of the floating culture contains many stem cells, the number of retinosphere that can be formed becomes high. When the stem cell contained in the cell at the time of start of the floating culture has high self-replication ability, the size (e.g., diameter) of the retinosphere that can be formed becomes large. The formed retinosphere can be differentiated into a retinal layer-specific neuron by reacting same with an appropriate factor.

In step (2) of the stem cell production method 1 of the present invention, SSEA-1 positive cells are collected from the cells obtained from "a cell aggregate comprising a ciliary marginal zone-like structure induced to differentiate from pluripotent stem cells" prepared as mentioned above.

Examples of the cells obtained from "a cell aggregate comprising a ciliary marginal zone-like structure induced to differentiate from pluripotent stem cells" include cells obtained by dispersing the above-mentioned "cell aggregate comprising a ciliary marginal zone-like structure induced to differentiate from pluripotent stem cells", cells obtained by dispersing a ciliary marginal zone-like structure separated from the aforementioned cell aggregate, and cells obtained by dispersing a retinosphere formed from the aforementioned cell aggregate or ciliary marginal zone-like structure. SSEA-1 positive cell is collected from such cells.

A method for separating a ciliary marginal zone-like structure from "a cell aggregate comprising a ciliary marginal zone-like structure induced to differentiate from pluripotent stem cells" can be similar to the method performed for the aforementioned step (1).

As a method of forming a retinosphere from the above-mentioned cell aggregate or ciliary marginal zone-like structure, a method including the aforementioned floating culture of the cell in step (1) can be mentioned.

As a method of dispersing a cell aggregate, a ciliary marginal zone-like structure or a retinosphere, the aforementioned dispersion treatment in step (1) can be mentioned.

A method for collecting SSEA-1 positive cells, a method using a flow cytometer and a method using magnetism can be mentioned. Examples of the method using a flow cytometer include a method including labeling an SSEA-1 positive cell with a fluorescence-labeled anti-SSEA-1 antibody, and selecting and collecting the cell by a flow cytometer. Examples of the method using magnetism include a method including labeling an SSEA-1 positive cell with a magnetized anti-SSEA-1 antibody, and selecting and collecting the cell by a magnetic cell separation apparatus (MACS).

As the anti-SSEA-1 antibody, any antibody can also be used as long as it recognizes SSEA-1 antigen. A commercially available anti-SSEA-1 antibody such as anti-SSEA-1 antibody of Chemicon, anti-SSEA-1 antibody of BD, anti-SSEA-1 antibody of Miltenyi Biotec etc. can also be utilized.

When SSEA-1 positive cell is to be separated, it may be separated by using, in addition to being SSEA-1 positive, being Rax positive or absence of pigmentation as an index.

The thus-collected SSEA-1 positive cell fraction contains a ciliary marginal zone stem cell. The collected SSEA-1 positive cell fraction can be differentiated into a retinal layer-specific neuron by reacting the cell with an appropriate factor.

In the stem cell production method 2 of the present invention, step (1) of the stem cell production method 1 of the present invention is performed. In the stem cell production method 2 of the present invention, as "cells obtained from a cell aggregate comprising a ciliary marginal zone-like structure induced to differentiate from pluripotent stem cells", cells obtained by dispersing a cell aggregate comprising a ciliary marginal zone-like structure induced to differentiate from pluripotent stem cells, or cells obtained by dispersing a ciliary marginal zone-like structure separated from the cell aggregate are used.

That is, the stem cell production method 2 of the present invention is a method for producing a ciliary marginal zone stem cell induced to differentiate from pluripotent stem cells, comprising performing a step of floating culturing cells obtained by dispersing:

a cell aggregate comprising a ciliary marginal zone-like structure induced to differentiate from pluripotent stem cells, or a ciliary marginal zone-like structure separated from the cell aggregate, thereby obtaining a retinosphere.

In the stem cell production method 3 of the present invention, step (2) of the stem cell production method 1 of the present invention is performed. In the stem cell production method 3 of the present invention, as "cells obtained from a cell aggregate comprising a ciliary marginal zone-like structure induced to differentiate from pluripotent stem cells", cells obtained by dispersing a cell aggregate comprising a ciliary marginal zone-like structure induced to differentiate from pluripotent stem cells, or cells obtained by dispersing a ciliary marginal zone-like structure separated from the cell aggregate are used.

That is, the stem cell production method 3 of the present invention is a method for producing a ciliary marginal zone stem cell induced to differentiate from pluripotent stem cells, comprising performing a step of collecting SSEA-1 positive cells from cells obtained by dispersing:

a cell aggregate comprising a ciliary marginal zone-like structure induced to differentiate from pluripotent stem cells, or a ciliary marginal zone-like structure separated from the cell aggregate.

In the stem cell production method 4 of the present invention, step (1) is performed followed by performing step (2) of the stem cell production method 1 of the present invention. As "cells obtained from a cell aggregate comprising a ciliary marginal zone-like structure induced to differentiate from pluripotent stem cells" in the step (1), cells obtained by dispersing a cell aggregate comprising a ciliary marginal zone-like structure induced to differentiate from pluripotent stem cells, or cells obtained by dispersing a ciliary marginal zone-like structure separated from the cell aggregate are used. As "cells obtained from a cell aggregate comprising a ciliary marginal zone-like structure induced to differentiate from pluripotent stem cells" in the step (2), cells obtained by dispersing the retinosphere obtained in the step (1) are used.

That is, the stem cell production method 4 of the present invention is a method for producing a ciliary marginal zone stem cell induced to differentiate from pluripotent stem cells, comprising performing (1) a step of floating culturing cells obtained by dispersing:
   a cell aggregate comprising a ciliary marginal zone-like structure induced to differentiate from pluripotent stem cells, or
   a ciliary marginal zone-like structure separated from the cell aggregate, thereby obtaining a retinosphere; and
(2) a step of collecting SSEA-1 positive cells from cells obtained by dispersing the retinosphere obtained by the step (1).

In the stem cell production method 5 of the present invention, step (2) is performed followed by performing step (1) of the stem cell production method 1 of the present invention. As "cells obtained from a cell aggregate comprising a ciliary marginal zone-like structure induced to differentiate from pluripotent stem cells" in the step (2), cells obtained by dispersing a cell aggregate comprising a ciliary marginal zone-like structure induced to differentiate from pluripotent stem cells, or cells obtained by dispersing a ciliary marginal zone-like structure separated from the cell aggregate are used. As "cells obtained from a cell aggregate comprising a ciliary marginal zone-like structure induced to differentiate from pluripotent stem cells" in the step (1), cells obtained by dispersing the cells collected in the step (2) are used.

That is, the stem cell production method 5 of the present invention is a method for producing a ciliary marginal zone stem cell induced to differentiate from pluripotent stem cells, comprising performing a step of collecting SSEA-1 positive cells from cells obtained by dispersing:
   a cell aggregate comprising a ciliary marginal zone-like structure induced to differentiate from pluripotent stem cells, or
   a ciliary marginal zone-like structure separated from the cell aggregate, and
   a step of floating culturing cells obtained by dispersing cells collected in the aforementioned step, thereby obtaining a retinosphere.

The retinosphere or SSEA-1 positive cell fraction obtained by any of the stem cell production methods 1 to 5 of the present invention (hereinafter sometimes referred to as the stem cell production method of the present invention) can be used as a cell population containing a ciliary marginal zone stem cell at a high proportion.

A retinal layer-specific neuron can be produced by culturing a ciliary marginal zone stem cell obtained by the stem cell production method of the present invention in the presence of one or more substance selected from the group consisting of substances inhibiting Notch signal, a retinoid and taurine.

Examples of the ciliary marginal zone stem cell include a ciliary marginal zone stem cell contained in the retinosphere obtained by the stem cell production method of the present invention and a ciliary marginal zone stem cell contained in the SSEA-1 positive cell fraction obtained by the stem cell production method of the present invention.

For example, the above-mentioned retinosphere or the above-mentioned SSEA-1 positive cell fraction is cultivated under conditions suitable for neuronal differentiation. A cell obtained by dispersing the above-mentioned retinosphere or the above-mentioned SSEA-1 positive cell fraction may be cultured similarly.

As a medium used for such culture, a serum-containing medium or serum-free medium each containing one or more substance selected from the group consisting of substances inhibiting the Notch signal, a retinoid and taurine can be mentioned. For example, the above-mentioned retinosphere, the above-mentioned SSEA-1 positive cell fraction, or a cell obtained by dispersing same may be cultured in a serum-free medium or serum-containing medium each supplemented with one or more substance selected from the group consisting of substances acting on the FGF signal transduction pathway and substances acting on the EGF signal transduction pathway for a given period, and cultured in a serum-free medium or serum-containing medium each supplemented with one or more substance selected from the group consisting of substances inhibiting Notch signal, a retinoid and taurine. These media may contain an additive such as B27 supplement (Invitrogen) as appropriate.

The "substance inhibiting the Notch signal" here may be any substance as long as it inhibits the activity of Notch signal and, for example, γ-secretase inhibitory substance, Notch receptor inhibitory substance, Dll inhibitory substance, and Hes inhibitory substance can be mentioned. As the aforementioned γ-secretase inhibitory substance, DAPT (N-[N-(3,5-difluorophenacetyl)-L-alanyl]-S-phenylglycine t-butyl ester) can be mentioned. When DAPT is used as a substance inhibiting the Notch signal, for example, it is added to a concentration of about 0.01 μM to about 100 μM.

As a culture material to be used for culturing a ciliary marginal zone stem cell, a floating culture material and an adhesion culture material can be mentioned. As a coating material of a culture dish for adhesion culture, poly-D-lysine, poly-L-lysine, polyornithine, laminin, entactin, Matrigel, or gelatin can be mentioned.

A ciliary marginal zone stem cell is cultured, for example, at 37° C., $CO_2$ concentration of 5%, and oxygen concentration of 20% to 40%.

Whether or not the cell obtained by the above-mentioned culture contains a retinal layer-specific neuron can be checked by, for example, examining the expression of a cell marker.

The present invention also includes use of ciliary marginal zone stem cells or retinal layer-specific neuron produced by the method of the present invention as a reagent for the evaluation of the toxicity or drug efficacy, use of ciliary marginal zone stem cells or retinal layer-specific neuron produced by the method of the present invention as a biological material for transplantation and so on.

The ciliary marginal zone stem cells or retinal layer-specific neuron produced by the method of the present invention can be used for screening for a therapeutic drug for a disease due to a disorder of retinal cell, a material for the study of diseases or a drug discovery material. In the evaluation of the toxicity or drug efficacy of a chemical substance and so on, the ciliary marginal zone stem cells or retinal layer-specific neuron produced by the method of the present invention is also utilizable for study of toxicity such as phototoxicity, neurotoxicity and so on, toxicity test and so on. For example, ciliary marginal zone stem cells or retinal layer-specific neuron produced by the method of the present invention is brought into contact with a test substance, and an influence of the substance on the cell is assayed, based on which the toxicity or drug efficacy of the substance is evaluated.

The ciliary marginal zone stem cells or retinal layer-specific neuron produced by the method of the present invention can be used as a biological material for transplantation used for supplementing a disordered tissue itself in a cell damage state (e.g., used for transplantation operation) and so on. For example, an effective amount of ciliary marginal zone stem cells or retinal layer-specific neuron, which is produced by the method of the present invention, is transplanted to a subject in need of the transplantation, whereby a disease due to a disorder of retinal tissue is treated.

EXAMPLES

The present invention is explained in more detail in the following by referring to Examples, which are not to be construed as limitative.

Example 1

Production of Cell Aggregate Comprising Ciliary Marginal Zone-Like Structure from Pluripotent Stem Cells RAX::GFP knock-in human ES cells (derived from KhES-1; Nakano, T. et al. Cell Stem Cell 2012, 10(6), 771-785) were cultured according to the methods described in "Proc. Natl. Acad. Sci. USA, 2006, 103(25), 9554-9559" and "Nat. Biotech., 2007, 25, 681-686". As the medium, DMEM/F12 medium (Sigma) supplemented with 20% KSR (Knockout Serum™ Replacement; Invitrogen), 0.1 mM 2-mercaptoethanol, 2 mM L-glutamine, 1× non-essential amino acid and 8 ng/ml bFGF was used.

The aforementioned cultured ES cells were singly dispersed in TrypLE Express (Invitrogen), and the singly dispersed ES cells were floated in a 100 μl serum-free medium to $1.2 \times 10^4$ cells per well of a non-cell adhesive 96-well culture plate (SUMILON spheroid plate, SUMITOMO BAKELITE CO., LTD.) to allow for rapid formation of an aggregate, which was subjected to culture at 37° C., 5% $CO_2$. The serum-free medium used then was a serum-free medium which was a 1:1 mixture of F-12 medium and IMDM medium supplemented with 10% KSR, 450 μM 1-monothioglycerol, 1× Chemically Defined Lipid Concentrate and 20 μM Y27632. BMP4 was added at a final concentration of 1.5 nM on day 6 from the start of the floating culture, and the floating culture was continued. A half amount of the culture medium in the well was exchanged every 3 days with the above-mentioned medium free of a substance acting on the BMP signal transduction pathway.

The thus-prepared cell aggregate comprising a retinal tissue on day 18 from the start of the floating culture was cultured in a serum-free medium supplemented with 3 μM CHIR99021 (a substance acting on the Wnt signal pathway) and 5 μM SU5402 (a substance inhibiting the FGF signal pathway) for 6 days, i.e., up to day 24 from the start of the floating culture. The serum-free medium used then was a serum-free medium which was DMEM/F-12 medium supplemented with 1% N2 supplement (Invitrogen).

A cell aggregate obtained on day 24 from the start of the floating culture was subjected to floating culture in a serum-containing medium (medium which is DMEM/F-12 medium supplemented with 10% fetal bovine serum, 1% N2 supplement, 0.5 μM retinoic acid and 100 μM taurine) free of a substance acting on the Wnt signal pathway and a substance inhibiting the FGF signal pathway under 40% $O_2$ conditions for 11 days further, i.e., up to day 35 from the start of the floating culture, and the obtained cell aggregate was observed under a fluorescence microscope. The phase-contrast image (A) and GFP fluorescence image (B) of the cell aggregate (on day 35 from the start of the floating culture) are shown in FIG. 1. It was found that Rax gene expression-positive neural retina and pigment-deposited retinal pigment epithelium were formed in the cell aggregate, and a ciliary marginal zone-like structure (arrow in the Figure) was formed in the boundary part thereof.

Example 2

Production of a Cell Aggregate Comprising a Ciliary Marginal Zone-Like Structure from Pluripotent Stem Cells Singly-dispersed RAX::GFP knock-in human ES cells prepared by the method described in Example 1 were floated in a 100 μl serum-free medium to $9 \times 10^3$ cells per well of a non-cell adhesive 96-well culture plate (SUMILON spheroid plate, SUMITOMO BAKELITE CO., LTD.), and floating-cultured at 37° C., 5% $CO_2$. The serum-free medium used then was a serum-free medium obtained by adding 20% KSR, 0.1 mM 2-mercaptoethanol, 1 mM pyruvic acid, 20 μM Y27632 and 3 μM IWR1e (a substance inhibiting on the Wnt signal pathway) to G-MEM medium. During the floating culture, GFR Matrigel™ (BD Biosciences) in an amount of 1/100 per volume was added from day 2 from the start of the floating culture. A fetal bovine serum in an amount of 1/10 per volume and 100 nM SAG (a substance acting on the Shh signal pathway) were added on day 12 from the start of the floating culture, and the floating culture was performed up to day 18 from the start of the floating culture.

A cell aggregate comprising a retinal tissue on day 18 from the start of the floating culture was subjected to floating culture in a serum-free medium supplemented with 3 μM CHIR99021 (a substance acting on the Wnt signal pathway) for 2 days, i.e., up to day 20 from the start of the floating culture. The serum-free medium used then was a serum-free medium which was DMEM/F-12 medium supplemented with 1% N2 supplement (Invitrogen).

Figure 2:
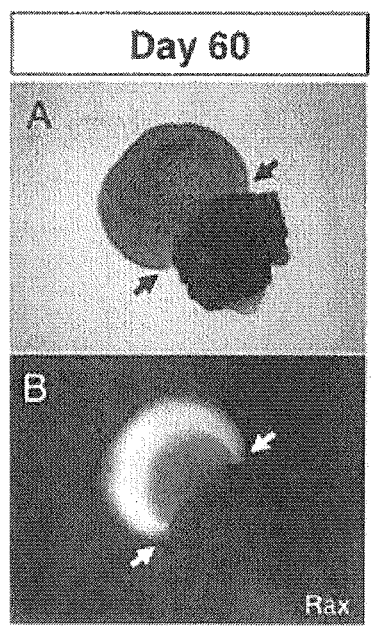
FIG. 2 shows a phase-contrast image (A) and a GFP fluorescence image (B) (Rax) of a cell aggregate comprising a ciliary marginal zone-like structure (day 60 from the start of floating culture).

A cell aggregate on day 20 from the start of the floating culture was subjected to floating culture in a serum-containing medium (medium which is DMEM/F-12 medium supplemented with 10% fetal bovine serum, 1% N2 supplement, 0.5 μM retinoic acid and 100 μM taurine) free of a substance acting on the Wnt signal pathway under 40% $O_2$ conditions for 40 days further, i.e., up to day 60 from the start of the floating culture, and the obtained cell aggregate was observed under a fluorescence microscope. The phase-contrast image (A) and GFP fluorescence image (B) of the cell aggregate (day 60 from the start of the floating culture) are shown in FIG. 2. It was found that Rax gene expression-positive neural retina and pigment-deposited retinal pigment epithelium were formed in the cell aggregate, and a ciliary marginal zone-like structure (arrow in the Figure) was formed in the boundary part thereof.

Example 3

Figure 3:
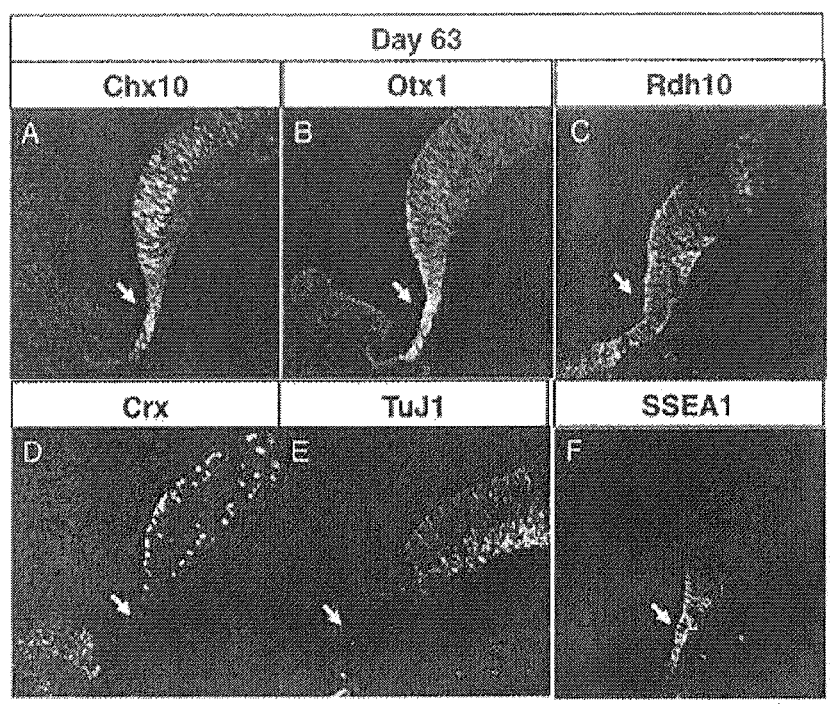
FIG. 3 shows stained images of cryosection of cell aggregate comprising a ciliary marginal zone-like structure (day 63 from the start of floating culture). "A" is an immunostained image of Chx10 positive cell, "B" is an immunostained image of Otx1 positive cell, "C" is an immunostained image of Rdh10 positive cell, "D" is an immunostained image of Crx positive cell, "E" is an immunostained image of TuJ1 positive cell, and "F" is an immunostained image of SSEA-1 positive cell.

Production of Cell Aggregate Comprising a Ciliary Marginal Zone-Like Structure from Pluripotent Stem Cells and Analysis of Marker Expression A cell aggregate on day 24 from the start of the floating culture, which was produced by the method described in Example 1, was subjected to floating culture in a serum-containing medium (medium which is DMEM/F-12 medium supplemented with 10% fetal bovine serum, 1% N2 supplement, 0.5 μM retinoic acid, and 100 μM taurine) free of a substance acting on the Wnt signal pathway and a substance inhibiting the FGF signal pathway further for 39 days, i.e., up to day 63 from the start of the floating culture under 40% $O_2$ conditions, and the obtained cell aggregate on day 63 from the start of the floating culture was fixed with 4% para-formaldehyde to prepare a cryosection. For the prepared cryosection, immunostaining of Chx10 which is one of neural retina progenitor cell markers (FIG. 3A), Otx1 which is one of ciliary marginal zone markers (FIG. 3B), Rdh10 which is one of ciliary marginal zone markers (FIG. 3C), Crx which is one of photoreceptor cell markers (FIG. 3D), or TuJ1 which is one of markers for nerve cell including ganglion cell (FIG. 3E). It was found that Chx10 positive (FIG. 3A), Otx1 positive (FIG. 3B) and Rdh10 positive (FIG. 3C) ciliary marginal zone-like structures (arrow in the Figure) were formed in the cell aggregate. The ciliary marginal zone-like structure (arrow in the Figure) was Crx negative (FIG. 3D) and TuJ1 negative (FIG. 3E).

The above-mentioned cryosection prepared from the cell aggregate on day 63 from the start of the floating culture was immunostained for SSEA-1. It was found that SSEA-1 was locally expressed in a ciliary marginal zone-like structure in the above-mentioned cell aggregate (FIG. 3F). Deposition of pigment was not observed in the SSEA-1 positive cell.

From the above results, it was found that Chx10 positive, Otx1 positive, Rdh10 positive, Crx negative, TuJ1 negative and SSEA-1 positive cell free of pigment deposition was present in the ciliary marginal zone-like structure contained in the above-mentioned cell aggregate on day 63 from the start of the floating culture.

Example 4

Separation of Ciliary Marginal Zone-Like Structure from Cell Aggregate Comprising Ciliary Marginal Zone-Like Structure A cell aggregate on day 24 from the start of the floating culture, which was produced by the method described in Example 1, was subjected to floating culture in a serum-containing medium (medium which is DMEM/F-12 medium supplemented with 10% fetal bovine serum, 1% N2 supplement, 0.5 µM retinoic acid, and 100 µM taurine) free of a substance acting on the Wnt signal pathway and a substance inhibiting the FGF signal pathway for 66 days, i.e., up to day 90 from the start of the floating culture under 40% $O_2$ conditions. A Rax positive neural retinal region and a ciliary marginal zone-like structure present in the boundary part of neural retina and retinal pigment epithelium were separately cut out from the cell aggregate obtained on day 90 from the start of the floating culture, by using scalpel and tweezers under observation with a fluorescence stereomicroscope.

Figure 4:
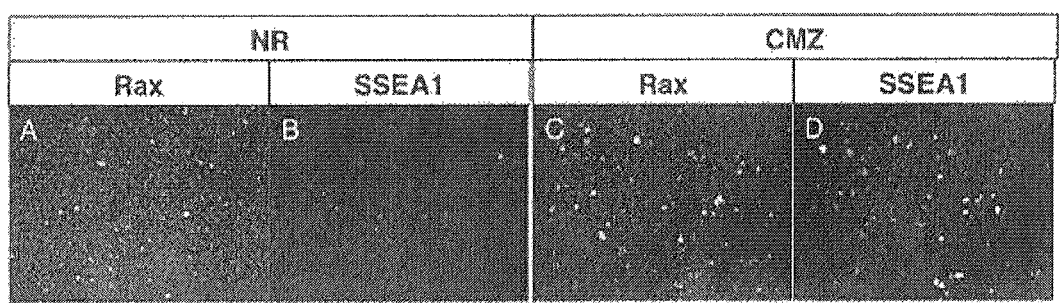
FIG. 4 shows fluorescence microscopic images of a cell obtained by dispersing a neural retinal region or a ciliary marginal zone-like structure separated from a cell aggregate comprising a ciliary marginal zone-like structure (day 90 from the start of floating culture). "A"(Rax) is a GFP fluorescence image of neural retinal region (NR), "B" (SSEA1) is an immunofluorescence stained image of a neural retinal region (NR) by using an anti-SSEA-1 antibody, "C"(Rax) is a GFP fluorescence image of a ciliary marginal zone-like structure (CMZ), and "D"(SSEA1) is an immunofluorescence stained image of a ciliary marginal zone-like structure (CMZ) by using an anti-SSEA-1 antibody.

The obtained neural retinal region and ciliary marginal zone-like structure were each dispersed in a dispersion containing papain (nerve cell dispersion, SUMITOMO BAKELITE) to prepare a cell suspension. Each cell suspension was immunostained with a fluorescence-labeled anti-SSEA-1 antibody (Anti-SSEA1, Cy3 conjugated; Chemicon) while the cells were viable, and observed by a fluorescence microscope. The fluorescence of expressed GFP was used as an index of Rax gene expression, and the fluorescence of Cy3 in the above-mentioned anti-SSEA-1 antibody was used as an index of SSEA-1 expression. The results are shown in FIG. 4. In the above-mentioned cell suspension prepared from the neural retinal region, the proportion of the Rax positive and SSEA-1 negative cells was about 80%, the proportion of the Rax positive and SSEA-1 positive cells was about 10%, and Rax negative cell was about 10% (FIG. 4A, B). In the above-mentioned cell suspension prepared from the ciliary marginal zone-like structure, the proportion of the Rax positive and SSEA-1 negative cells was about 30%, the proportion of the Rax positive and SSEA-1 positive cells was about 50%, and the Rax negative cell was about 20% (FIG. 4C, D). It was found that the Rax positive and SSEA-1 positive cells contained in the aforementioned cell aggregate can be purified by an operation to cut out a ciliary marginal zone-like structure from the cell aggregate.

Example 5

Analysis of Pigment Deposition in Rax Positive and SSEA-1 Positive Cells Contained in Cell Aggregate Comprising Ciliary Marginal Zone-Like Structure Retinal pigment epithelium and a ciliary marginal zone-like structure were simultaneously cut out by a method similar to that in Example 4 from the cell aggregate on day 90 from the start of the floating culture and prepared by the method described in Example 4, by using scalpel and tweezers under observation with a fluorescence stereomicroscope.

Figure 5:
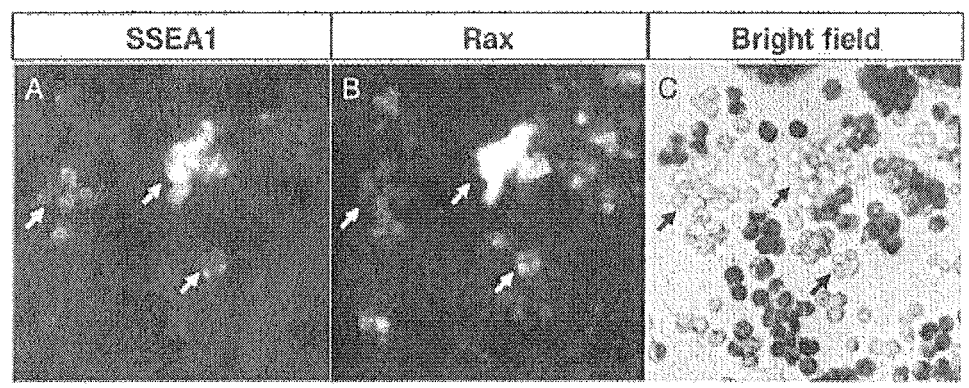
FIG. 5 shows fluorescence microscopic images of a cell obtained by dispersing retinal pigment epithelium and a ciliary marginal zone-like structure separated from a cell aggregate comprising a ciliary marginal zone-like structure (day 90 from the start of floating culture). "A"(SSEA1) is immunofluorescence stained image by using an anti-SSEA-1 antibody, "B"(Rax) is a GFP fluorescence image, and "C"(Bright field) is a bright field image.

The obtained retinal pigment epithelium and ciliary marginal zone-like structure were dispersed in a dispersion containing papain by a method similar to that in Example 4 to give a cell suspension. The obtained cell suspension was immunostained with a fluorescence labeled anti-SSEA-1 antibody (Anti-SSEA1, Cy3 conjugated; Chemicon) while the cells were viable, and observed by a fluorescence microscope. The results are shown in FIG. 5. Pigment deposition was not observed in SSEA-1 positive (FIG. 5A, arrow) and Rax positive cells (FIG. 5B, arrow) (FIG. 5C, arrow).

Example 6

Retinosphere Formation from Cell Aggregate Comprising Ciliary Marginal Zone-Like Structure A cell aggregate on day 24 from the start of the floating culture, which was produced by the method described in Example 1, was subjected to floating culture in a serum-containing medium (medium which is DMEM/F-12 medium supplemented with 10% fetal bovine serum, 1% N2 supplement, 0.5 µM retinoic acid, and 100 µM taurine) free of a substance acting on the Wnt signal pathway and a substance inhibiting the FGF signal pathway further for 39 days, i.e., up to day 63 from the start of the floating culture under 40% $O_2$ conditions. The obtained cell aggregate on day 63 from the start of the floating culture was dispersed in a dispersion containing papain by a method similar to that in Example 4 to give a cell pension. The cells contained in the obtained cell suspension were subjected to gloating—culture for 10 days in a serum-free medium which is DMEM/F-12 medium supplemented with bFGF (20 ng/ml), EGF (20 ng/ml), heparin (5 µg/ml), B27 (50-fold diluted) at a cell density of $1\times10^5$ cells/ml. As a result, a spherical cell aggregate (retinosphere) was formed. It was found that the above-mentioned cell aggregate on day 63 from the start of the floating culture contained a cell having a proliferative capacity.

Figure 6:
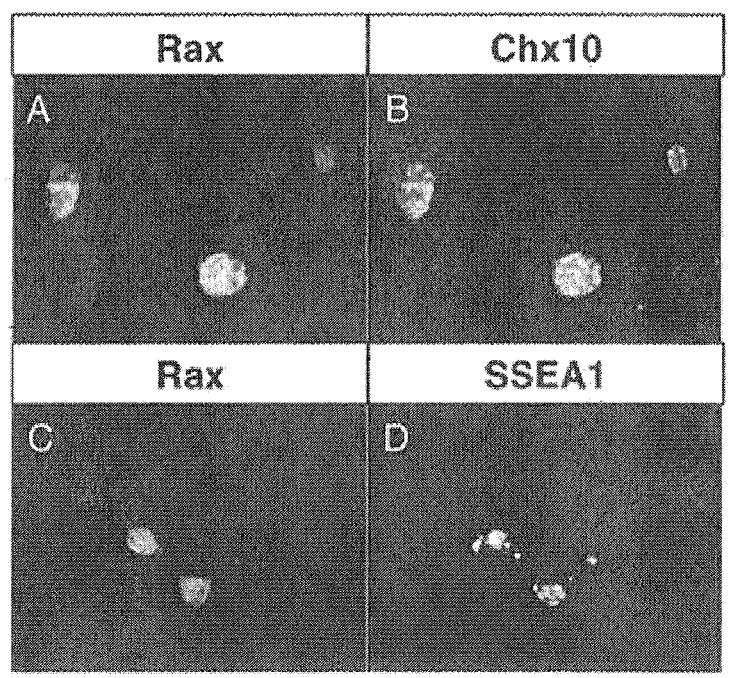
FIG. 6 shows fluorescence microscopic images of retinosphere formed by dispersing a cell aggregate comprising a ciliary marginal zone-like structure (day 63 from the start of floating culture) and subjecting the obtained cells to floating culture. "A" and "C"(Rax) are GFP fluorescence images, "B"(Chx10) is an immunofluorescence stained image by using an anti-Chx10 antibody, and "D"(SSEA1) is an immunofluorescence stained image by using an anti-SSEA-1 antibody.

The obtained retinosphere was fixed with 4% para-formaldehyde, the expression of Rax gene was examined using the expression of GFP as an index, Expressions of Chx10 and SSEA-1 were examined by immunostaining. The results are shown in FIG. 6. It was found that about 90% of the cells forming the aforementioned retinosphere were Rax positive (FIG. 6A) and Chx10 positive (FIG. 6B), namely, cells expressing retina progenitor cell marker and neural retina progenitor cell marker. The above-mentioned retinosphere contained about 40% of Rax positive (FIG. 6C) and SSEA-1 positive (FIG. 6D) cells.

In the above-mentioned culture example, a retinosphere containing about 50 to 500 cells was formed from 1 to about 10 cells contained in the above-mentioned cell suspension as a starting material. Accordingly, about 20 to 200 Rax positive and SSEA-1 positive cells were formed from 1 to about 10 cells contained in the above-mentioned cell suspension. It was found that floating culture of cells obtained from the above-mentioned cell aggregate containing a ciliary marginal zone-like structure can efficiently produce a Rax positive and SSEA-1 positive cell.

Example 7

Formation of Retinosphere from Ciliary Marginal Zone-Like Structure Separated from Cell Aggregate Comprising Ciliary Marginal Zone-Like Structure A cell aggregate on day 24 from the start of the floating culture, which was produced by the method described in Example 1, was subjected to floating culture in a serum-containing medium (medium which is DMEM/F-12 medium supplemented with 10% fetal bovine serum, 1% N2 supplement, 0.5 µM retinoic acid, and 100 µM taurine) free of a substance acting on the Wnt signal pathway and a substance inhibiting the FGF signal pathway further for 46 days, i.e., up to day 70 from the start of the floating culture under 40% $O_2$ conditions. A neural retinal region and a ciliary marginal zone-like structure were separately cut out from the cell aggregate on day 70 from the start of the floating culture, by using scalpel and tweezers under observation with a fluorescence stereomicroscope.

Figure 7:
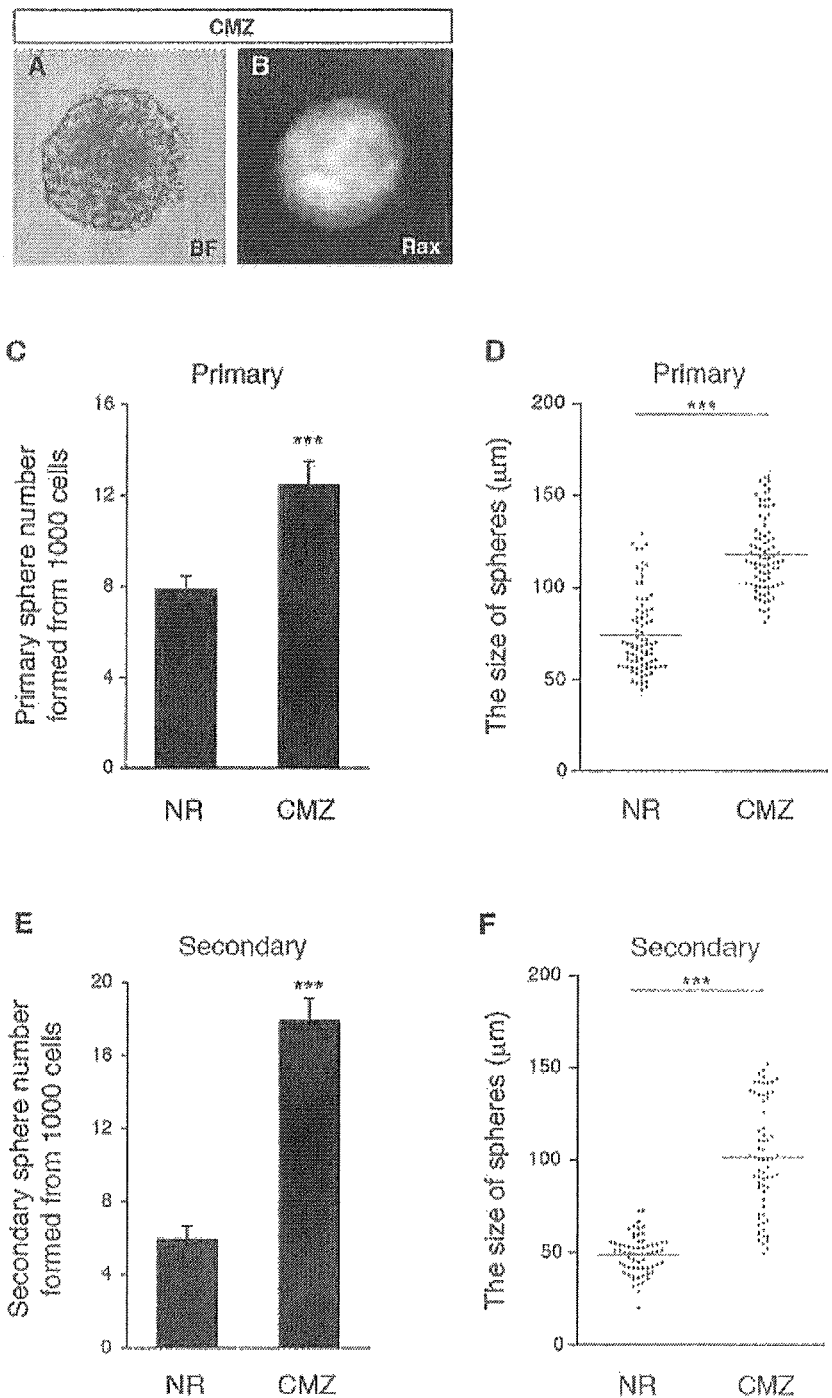
FIG. 7 shows analysis results of retinosphere formed by dispersing neural retinal region (NR) or ciliary marginal zone-like structure (CMZ) separated from a cell aggregate (day 70 from the start of floating culture), and subjecting the obtained cells to floating culture. "A" and "B" are fluorescence microscopic images of retinospheres formed from a ciliary marginal zone-like structure (CMZ), "A"(BF) is a bright field image, and "B"(Rax) is a GFP fluorescence image. "C" shows formation number of primary retinosphere, and "E" shows formation number of secondary retinosphere. "D" shows diameter distribution of primary retinosphere, and "F" shows diameter distribution of secondary retinosphere.

The obtained neural retinal region and ciliary marginal zone-like structure were each dispersed in a dispersion containing papain, by a method similar to that in Example 4 to give cell suspensions. The cells contained in each cell suspension were seeded in a flat-bottomed 96 well dish (manufactured by Nunc) low adhesion treated with a serum-free medium which is DMEM/F-12 medium supplemented with bFGF (20 ng/ml), EGF (20 ng/ml), heparin (5 µg/ml), B27 (50-fold diluted) at 1000 cells per well ($5 \times 10^3$ cells/ml), and floating culture was performed at 37° C. for 10 days to form a retinosphere. It was found that the formed retinosphere was Rax positive (FIG. 7B) and free of pigment deposition (FIG. 7A). The number and size (diameter) of the formed retinosphere (primary retinosphere) are shown in FIGS. 7C and D. It was found that the above-mentioned neural retinal region and a ciliary marginal zone-like structure contained a cell having a self-replication ability. The cells obtained from a ciliary marginal zone-like structure (CMZ) showed higher retinosphere formation efficiency as compared to the cells obtained from neural retinal region (NR) (FIG. 7C). It was found that the cells obtained from a ciliary marginal zone-like structure (CMZ) have a larger size of the formed retinosphere as compared to the cells obtained from neural retinal region (NR) (FIG. 7D). The above-mentioned retinosphere formed from the ciliary marginal zone-like structure contained a Rax positive and SSEA-1 positive cell. It was found that floating culture of cells obtained from a ciliary marginal zone-like structure separated from the above-mentioned cell aggregate can efficiently produce a Rax positive and SSEA-1 positive cell.

Cell suspensions of the above-mentioned retinosphere formed from a cell obtained by dispersing a neural retinal region, and of the above-mentioned retinosphere formed from a cell obtained by dispersing the ciliary marginal zone-like structure were prepared, and cultured by the method described in Example 6 to form a secondary retinosphere. The number and size (diameter) of the retinosphere formed are shown in FIGS. 7E and F. It was found that the above-mentioned primary retinosphere contained a cell having self-replication ability. The cells derived from the ciliary marginal zone-like structure (CMZ) showed higher formation efficiency of the secondary retinosphere (FIG. 7E) as compared to the cells derived from the neural retinal region (NR). It was found that the cells obtained from the ciliary marginal zone-like structure (CMZ) have a larger size of the secondary retinosphere formed as compared to the cells obtained from the neural retinal region (NR) (FIG. 7F). The above-mentioned secondary retinosphere formed from the cells derived from a ciliary marginal zone-like structure contained a Rax positive and SSEA-1 positive cell. It was found that Rax positive and SSEA-1 positive cells can be expanded by repeating the retinosphere formation culture as described above.

Example 8

Figure 8:
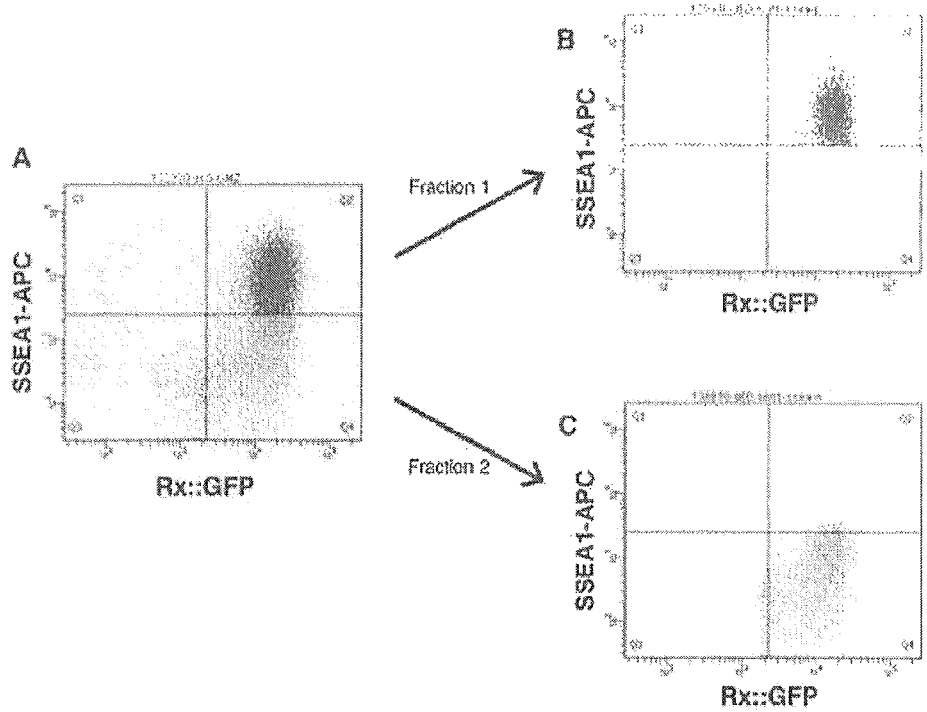
FIG. 8 "A" shows the results obtained by dispersing a ciliary marginal zone-like structure separated from a cell aggregate (day 60 from the start of floating culture), immunostaining the obtained cell suspension with a fluorescence-labeled SSEA-1 antibody, and performing FACS analysis by using a cell sorter.

Collection of SSEA-1 Positive Cell from Ciliary Marginal Zone-Like Structure Separated from Cell Aggregate Comprising Ciliary Marginal Zone-Like Structure A cell aggregate on day 24 from the start of the floating culture, which was produced by the method described in Example 1, was subjected to floating culture in a serum-containing medium (medium which is DMEM/F-12 medium supplemented with 10% fetal bovine serum, 1% N2 supplement, 0.5 µM retinoic acid, and 100 µM taurine) free of a substance acting on the Wnt signal pathway and a substance inhibiting the FGF signal pathway further for 36 days, i.e., up to day 60 from the start of the floating culture under 40% $O_2$ conditions. A ciliary marginal zone-like structure was cut out from the obtained cell aggregate on day 60 from the start of the floating culture, dispersed in a dispersion containing papain by a method similar to that in Example 4 to give a cell suspension. The obtained cell suspension was immunostained with a fluorescence labeled anti-SSEA-1 antibody (SSEA1-APC, manufactured by BD) while the cells were viable, and FACS analyzed by a cell sorter (ARIA2, manufactured by BD). The results are shown in FIG. 8. It was found that about 50% of the cells contained in the above-mentioned cell suspension were Rax positive and SSEA-1 positive (FIG. 8A). It was found that a Rax positive and SSEA-1 positive cell having a purity of about 50% can be produced by cutting out the aforementioned ciliary marginal zone-like structure from the above-mentioned a cell aggregate.

Using a cell sorter (ARIA2, manufactured by BD), Rax positive and SSEA-1 positive cells (FIG. 8A, Q2), and Rax negative and SSEA-1 positive cells (FIG. 8A, Q4) could be fractionated from the above-mentioned cell suspension. Rax positive and SSEA-1 positive cell fraction (Fraction 1) and Rax negative and SSEA-1 positive cell fraction (Fraction 2) were collected and analyzed by FACS. It was found that, of the cells contained in Fraction 1, 87% was Rax positive and SSEA-1 positive (FIG. 8B) and, of the cells contained in Fraction 2, 82% was Rax positive and SSEA-1 negative (FIG. 8C). It was found that Rax positive and SSEA-1 positive cells having a purity of about 87% can be produced by collecting the aforementioned ciliary marginal zone-like structure from a cell aggregate comprising a ciliary marginal zone-like structure and dispersing same therein, and collecting SSEA-1 positive cells from the obtained cell suspension.

Example 9

Figure 9:
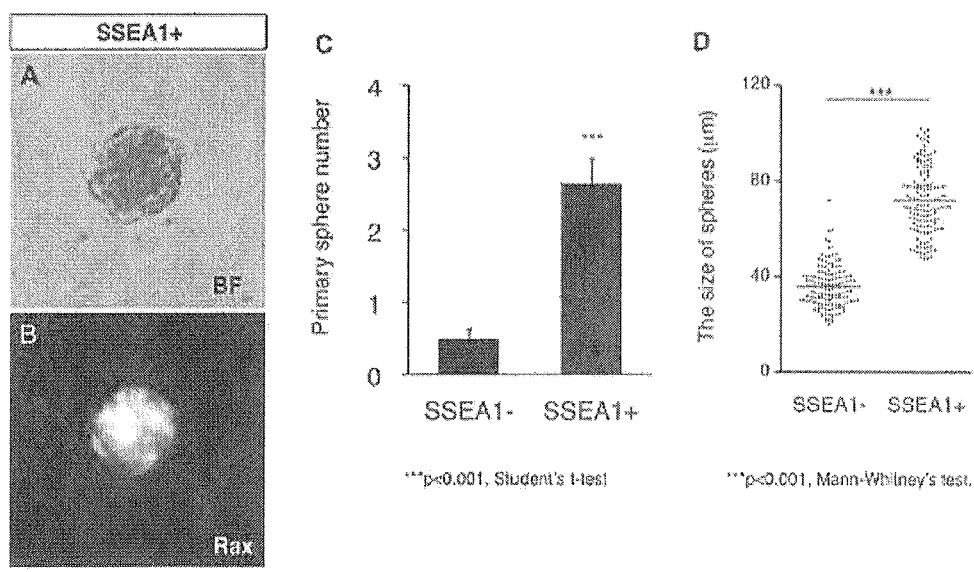
FIG. 9 shows analysis results of a retinosphere formed by dispersing a ciliary marginal zone-like structure separated from a cell aggregate (day 60 from the start of floating culture), separating Rax positive and SSEA-1 positive cell fraction (SSEA1+), and Rax positive and SSEA-1 negative cell fraction (SSEA1−) from the obtained cell suspension, and subjecting the separated cell fractions to floating culture. "A" and "B" are fluorescence microscopic images of the retinosphere formed from a Rax positive and SSEA1 positive cell fraction (SSEA1+), "A"(BF) is a bright field image, and "B"(Rax) is a GFP fluorescence image. "C" shows formation number of retinospheres. "D" shows diameter distribution of formed retinospheres.

Collection of SSEA-1 Positive Cell from Ciliary Marginal Zone-Like Structure Separated from Cell Aggregate Comprising Ciliary Marginal Zone-Like Structure and Formation of Retinosphere from Collected Cells A retinosphere was formed by culturing, according to the method described in Example 7, each of Rax positive and SSEA-1 positive cell fraction and a Rax positive and SSEA-1 negative cell fraction sorted by a cell sorter and according to the method described in Example 8. The retinosphere formed was Rax positive (FIG. 9B), and free of pigment deposition (FIG. 9A). The number and size (diameter) of the retinosphere formed are shown in FIGS. 9C and D. It was found that a retinosphere can be formed with higher efficiency from the Rax positive and SSEA-1 positive cell fraction, as compared to the Rax positive and SSEA-1 negative cell fraction (FIG. 9C). It was found that a retinosphere having a larger size can be formed from the Rax positive and SSEA-1 positive cell, as compared to the Rax positive and SSEA-1 negative cell (FIG. 9D). Furthermore, it was observed that the retinosphere formed from the Rax positive and SSEA-1 positive cell contained 80% or more of the Rax positive and SSEA-1 positive cells. It was found that the Rax positive and SSEA-1 positive cells produced by the above-mentioned method contains higher number of cells having self-replication ability than the Rax positive and SSEA-1 negative cells, and the Rax positive and SSEA-1 positive cells can be expanded by retinosphere formation culture.

Example 10

Improvement of Retinosphere Production Efficiency by the Addition of ROCK Inhibitor A cell aggregate on day 24 from the start of the floating culture and prepared by the method described in Example 1 was subjected to floating culture in a serum-containing medium (medium which is DMEM/F-12 medium supplemented with 10% fetal bovine serum, 1% N2 supplement, 0.5 µM retinoic acid and 100 taurine) free of a substance acting on the Wnt signal pathway and a substance inhibiting the FGF signal pathway under 40% $O_2$ conditions further for 39 days, i.e., up to day 63 from the start of the floating culture. The obtained cell aggregate on day 63 from the start of the floating culture was dispersed in a dispersion containing papain by a method similar to that in Example 4 to give a cell suspension. The cells contained in the obtained cell suspension were subjected to floating culture for 10 days in a serum-free medium which is DMEM/F-12 medium supplemented with bFGF (20 ng/ml), EGF (20 ng/ml), heparin (5 µg/ml), B27 (50-fold diluted), in the presence or absence of 10 µM Y-27632 (ROCK inhibitor) at a cell density of $1\times10^5$ cells/ml. As a result, spherical cell aggregates (retinospheres) were formed. In this case, 1300 retinospheres were formed in the absence of Y-27632, and 1976 retinospheres were formed in the presence of Y-27632. That is, it was found that addition of a ROCK inhibitor increases efficiency of retinosphere formation.

Example 11

Production of Photoreceptor Cell from Retinosphere

Figure 10:
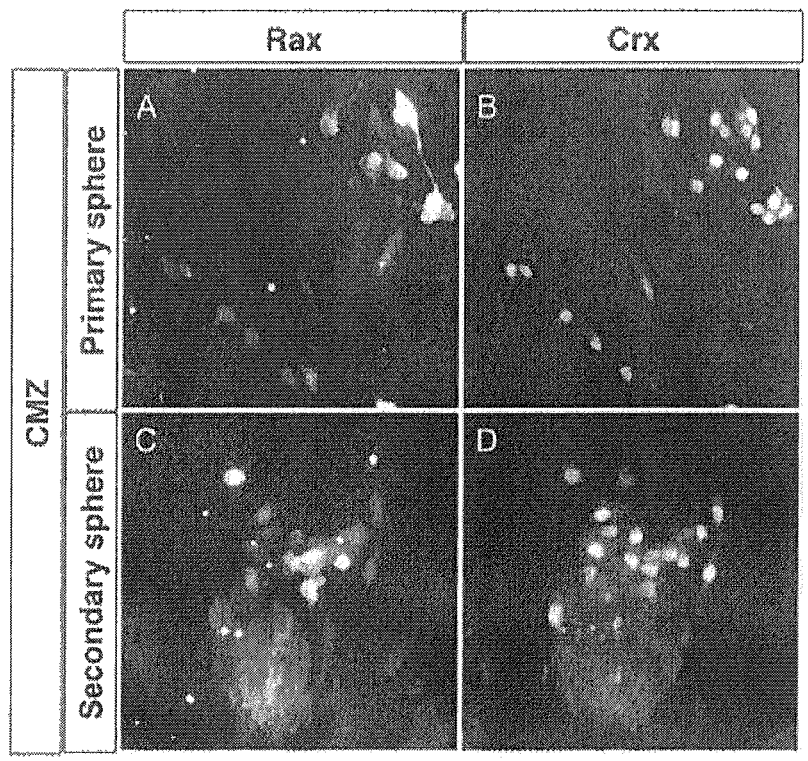
FIG. 10 shows fluorescence microscopic images of cells obtained by differentiating from a retinosphere formed by dispersing a ciliary marginal zone-like structure separated from a cell aggregate comprising a ciliary marginal zone-like structure (day 90 from the start of floating culture), and subjecting the obtained cells to floating culture. "A" and "B" are images of cells differentiated from the primary retinosphere, and "C" and "D" are images of cells differentiated from the secondary retinosphere. "A" and "C"(Rax) are GFP fluorescence images, and "B" and "D"(Crx) are immunofluorescence stained images by using an anti-Crx antibody.

Primary retinosphere and secondary retinosphere were formed by the method described in Example 7 from a ciliary marginal zone-like structure prepared by the method described in Example 4. The obtained primary retinosphere and secondary retinosphere were each seeded in a cell culture dish coated with poly-D-lysine and laminin, cultured for 4 days in a serum-free medium (medium which is DMEM/F-12 medium supplemented with bFGF (20 ng/ml), EGF (20 ng/ml), B27 (50-fold diluted)), and cultured for 10 days in a serum-containing medium (medium which is DMEM/F-12 medium supplemented with 10% fetal bovine serum, B27, 0.5 µM retinoic acid, 100 µM taurine and 10 µM DAPT) under the conditions of 40% $O_2$, 5% $CO_2$, 37° C. The obtained cells were fixed with para-formaldehyde, and a GFP fluorescence image showing the expression of Rax gene and an immunostained image by using an antibody against Crx which is one of the photoreceptor cell markers were observed. The results are shown in FIG. 10. It was found that from each of the above-mentioned primary retinosphere and secondary retinosphere, Rax positive (FIGS. 10A and C) and Crx positive (FIGS. 10B and D) photoreceptor cellscan be differentiated.

Example 12

Production of Amacrine Cell, Ganglion Cell from Retinosphere

Figure 11:
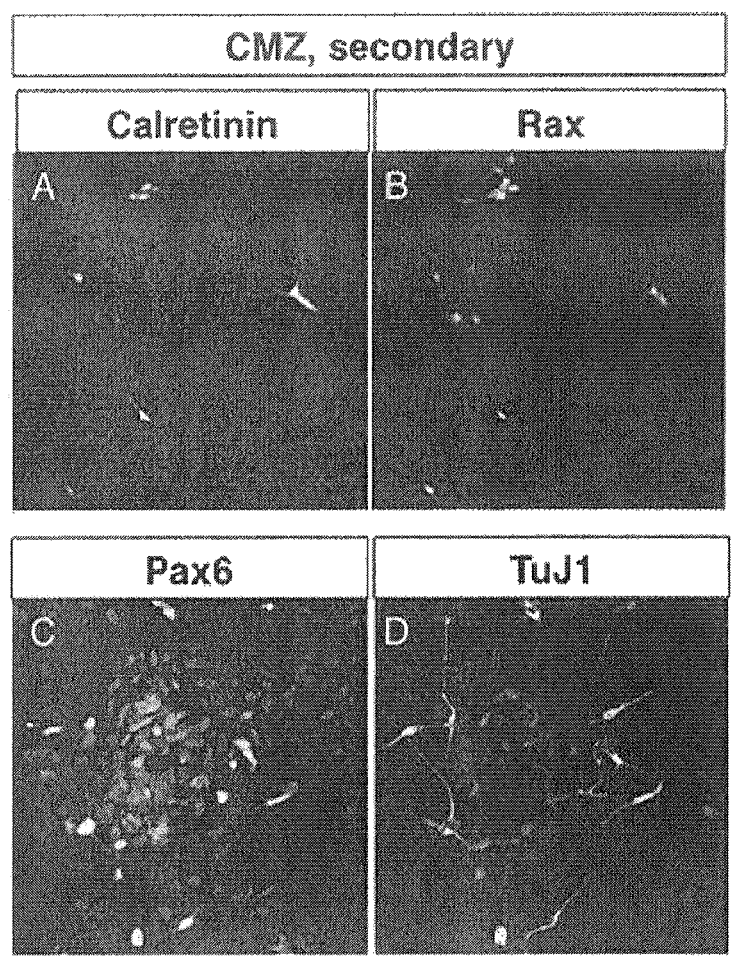
FIG. 11 shows fluorescence microscopic images of cells obtained by differentiating from a secondary retinosphere formed by dispersing a ciliary marginal zone-like structure separated from a cell aggregate comprising a ciliary marginal zone-like structure (day 60 from the start of floating culture), and subjecting the obtained cells to floating culture. "A"(Calretinin) is an immunofluorescence stained image by using an anti-Calretinin antibody, "B"(Rax) is a GFP fluorescence image, "C"(Pax6) is an immunofluorescence stained image by using an anti-Pax6 antibody, and "D"(TuJ1) is an immunofluorescence stained image by using an anti-TuJ1 antibody.

Primary retinosphere and secondary retinosphere were formed by the method described in Example 7 from a ciliary marginal zone-like structure prepared by the method described in Example 4. The obtained secondary retinosphere was seeded in a cell culture dish coated with poly-D-lysine and laminin, cultured for 2 days in a serum-free medium (medium which is DMEM/F-12 medium supplemented with bFGF (20 ng/ml), EGF (20 ng/ml), B27 (50-fold diluted)), and cultured for 10 days in a serum-containing medium (medium which is DMEM/F-12 medium supplemented with 10% fetal bovine serum, B27, 0.5 µM retinoic acid, 100 µM taurine and 10 µM DAPT) under the conditions of 40% $O_2$, 5% $CO_2$, 37° C. The obtained cells were fixed with para-formaldehyde, and a GFP fluorescence image showing the expression of Rax gene (FIG. 11B), an immunostained image using an antibody against Calretinin which is one of the amacrine cell markers (FIG. 11A), and immunostained images each using an antibody against Pax6 and TuJ1 which are co-positive markers to ganglion cells (FIGS. 11C and D) were observed. The results are shown in FIG. 11. It was found that from the above-mentioned secondary retinosphere, Calretinin positive amacrinee cells (FIGS. 11A, B), and Pax6 and TuJ1 positive ganglion cells (FIGS. 11C, D) can be differentiated.

Example 13

Figure 12:
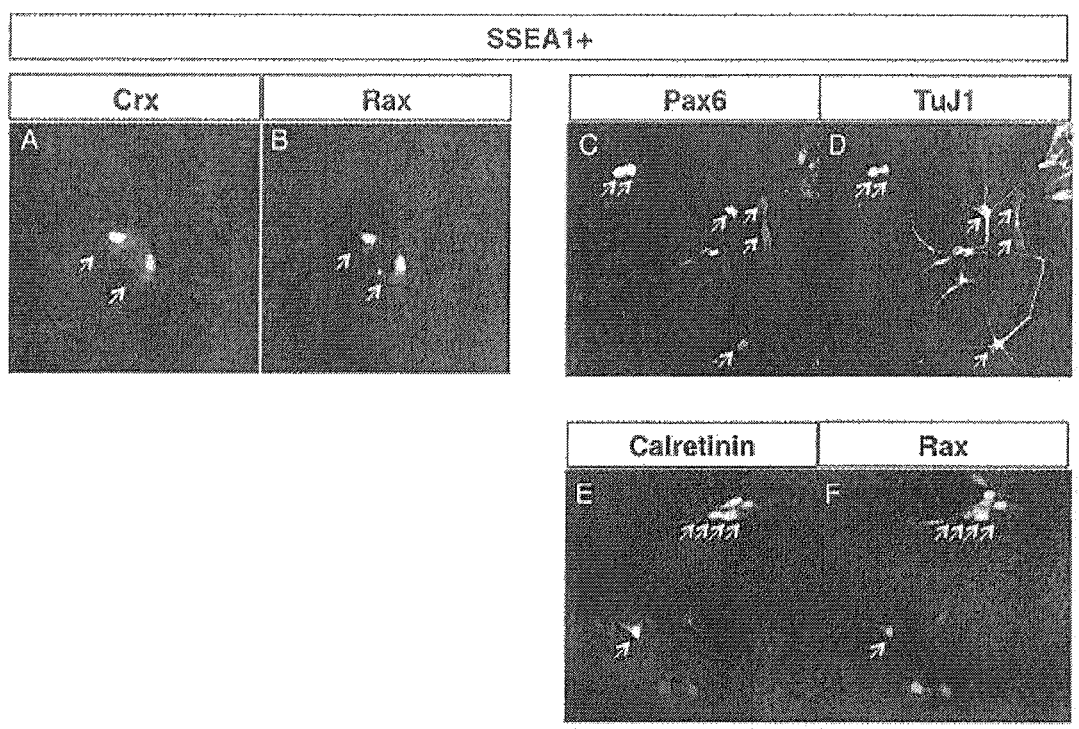
FIG. 12 shows fluorescence microscopic images of cells obtained by differentiating from a retinosphere formed by dispersing a Rax positive and SSEA1 positive cell separated from a ciliary marginal zone-like structure separated from a cell aggregate comprising a ciliary marginal zone-like structure (day 54 from the start of floating culture), and subjecting the obtained cells to floating culture. "A"(Crx) is an immunofluorescence stained image by using an anti-Crx antibody, "B" and "F"(Rax) are GFP fluorescence images, "C"(Pax6) is an immunofluorescence stained image by using an anti-Pax6 antibody, "D"(TuJ1) is an immunofluorescence stained image by using an anti-TuJ1 antibody, and "E" (Calretinin) is an immunofluorescence stained image by using an anti-Calretinin antibody.

Production of Photoreceptor Cell, Amacrine Cell, and Ganglion Cell from Retinosphere Formed from SSEA1 Positive Cell Retinospheres were formed from a ciliary marginal zone-like structure prepared by the method described in Example 4, by culturing, by the method described in Example 7, the Rax positive and SSEA-1 positive cell fraction sorted by a cell sorter and according to the method described in Example 8. The obtained retinospheres were each seeded in a cell culture dish coated with poly-D-lysine and laminin, cultured for 2 days in a serum-free medium (medium which is DMEM/F-12 medium supplemented with bFGF (20 ng/ml), EGF (20 ng/ml), B27 (50-fold diluted)), and cultured for 10 days in a serum-containing medium (medium which is DMEM/F-12 medium supplemented with 10% fetal bovine serum, B27, 0.5 µM retinoic acid, 100 µM taurine and 10 µM DAPT) under the conditions of 40% $O_2$, 5% $CO_2$, 37° C. The obtained cells were fixed with pareformaldehyde, and GFP fluorescence images showing the expression of Rax gene (FIGS. 12B, F), and immunostained images using an antibody against one of the photoreceptor cell markers, Crx (FIG. 12A), one of the amacrine cell markers, Calretinin (FIG. 12E), Pax6 and TuJ1 which are co-positive markers to ganglion cells (FIGS. 12C and D) were observed. The results are shown in FIG. 12. It was found that from the above-mentioned retinospheres, Rax positive and Crx positive photoreceptor cells (FIGS. 12A, B, arrow), Calretinin positive amacrine cells (FIGS. 12E, F, arrow), and Pax6 and TuJ1 positive ganglion cells (FIGS. 12C, D, arrow) can be differentiated.

Example 14

Collection of SSEA-1 Positive Cell from Ciliary Marginal Zone-Like Structure Separated from Cell Aggregate Comprising Ciliary Marginal Zone-Like Structure and Formation of Retinosphere from Collected Cells A cell aggregate on day 24 from the start of the floating culture, which was produced by the method described in Example 1, was subjected to floating culture in a serum-containing medium (medium which is DMEM/F-12 medium supplemented with 10% fetal bovine serum, 1% N2 supplement, 0.5 µM retinoic acid, and 100 µM taurine) free of a substance acting on the Wnt signal pathway and a substance inhibiting the FGF signal pathway further for 55 days, i.e., up to day 79 from the start of the floating culture under 40% $O_2$ conditions. A ciliary marginal zone-like structure was cut out from the obtained cell aggregate on day 79 from the start of the floating culture and dispersed in a dispersion containing papain by a method similar to that in Example 4 to give a cell suspension. The obtained cell suspension (unsorted fraction) was immunostained with a magnetic bead-labeled anti-SSEA-1 antibody (manufactured by Miltenyi Biotec) while the cells were viable, and an SSEA-1 positive cell fraction and an SSEA-1 negative cell fraction were collected using a magnetic cell separation apparatus (MACS, manufactured by Miltenyi Biotec).

The obtained SSEA-1 positive cell fraction and SSEA-1 negative cell fraction were each analyzed by FACS by the method described in Example 8, and it was found that 64% of the cells contained in the SSEA-1 positive cell fraction were SSEA-1 positive cells, and 5% of the cells contained in the SSEA-1 negative cell fraction were SSEA-1 positive cells. It was found that collecting the aforementioned ciliary marginal zone-like structure from the cell aggregate comprising the ciliary marginal zone-like structure and dispersing same, followed by collecting an SSEA-1 positive cell fraction from the resulting cell suspension, can result in producing SSEA-1 positive cells having a purity of about 64%.

Figure 13:
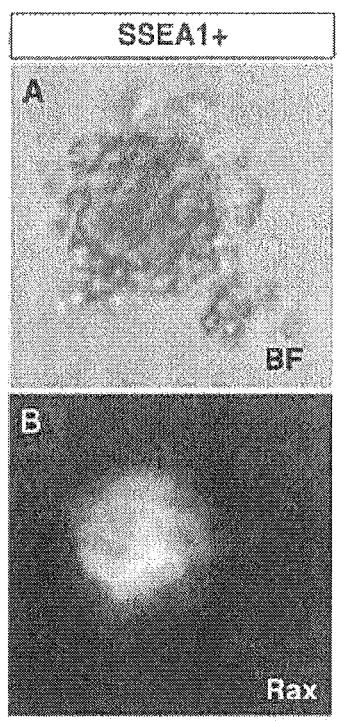
FIG. 13 shows analysis results of a retinosphere formed by dispersing a ciliary marginal zone-like structure separated from a cell aggregate (day 79 from the start of floating culture), separating SSEA-1 positive cell fraction and SSEA-1 negative cell fraction from the obtained cell suspension, and subjecting each of a cell suspension before fractionation, m separated SSEA-1 positive cell fraction, and separated SSEA-1 negative cell fraction to suspension growth culture. "A" and "B" are fluorescence microscopic images of retinosphere formed from SSEA-1 positive cell fraction, "A"(BF) is a bright field image, and "B"(Rax) is a GFP fluorescence image. "C" is a formation number of retinospheres. "Unsorted" is the number of retinospheres formed from a cell suspension before fractionation, "SSEA1$^+$" is the number of retinospheres formed from SSEA-1 positive cell fraction, and "SSEA1$^-$" is the number of retinospheres formed from SSEA-1 negative cell fraction.
Figure 13:
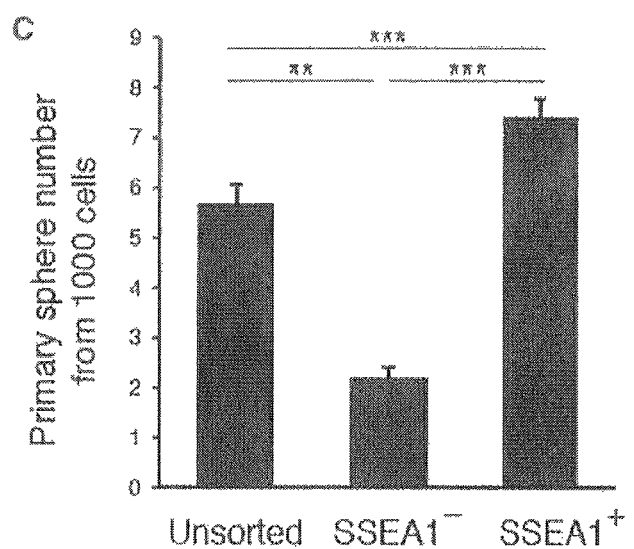

Retinospheres were formed by culturing the aforementioned unsorted fraction, SSEA-1 positive cell fraction, and SSEA-1 negative cell fraction by the method described in Example 7. The retinospheres formed were Rax positive (FIG. 13B), and free of pigment deposition (FIG. 13A). The number of the retinospheres formed is shown in FIG. 13C. It was found that the number of the retinospheres formed from SSEA-1 negative cell fraction was smaller (FIG. 13C, "SSEA1−") and the number of the retinospheres formed from SSEA-1 positive cell fraction was higher (FIG. 13C, "SSEA1+") than the number of the retinospheres formed from the unsorted fraction (FIG. 13C, "Unsorted"). It was found that the retinosphere formed from SSEA-1 positive cell fraction has a larger size as compared to the retinosphere formed from the SSEA-1 negative cell fraction. It was observed that the retinosphere formed from SEA-1 positive cell fraction contained 80% or more of the Rax positive and SSEA-1 positive cells.

It was found that the SSEA-1 positive cell fraction produced by the above-mentioned method contained higher number of cells having self-replication ability as compared to the SSEA-1 negative cell fraction.

This application is based on a patent application No. 2014-006464 filed in Japan (filing date: Jan. 17, 2014), the contents of which are incorporated in full herein.

INDUSTRIAL APPLICABILITY

According to the present invention, a tissue stem cell having differentiation potency into a retinal cell and self-replication ability can be efficiently produced with high purity.

The invention claimed is:
1. A method for producing a ciliary marginal zone stem cell, comprising:
performing steps (A) and (B):
(A) subjecting pluripotent stem cells to floating culture in a serum-free medium to form an aggregate of pluripotent stem cells, and
(B) performing floating culture of the aggregate formed in step (A) in a serum-free medium or serum-containing medium each free of a substance capable of enhancing signal transduction mediated by Sonic hedgehog and containing a substance capable of enhancing signal transduction mediated by BMP to produce a cell aggregate comprising a retinal tissue,
followed by performing step (i) or (ii):
(i) culturing a cell aggregate comprising a retinal tissue as produced in step (B) in which Chx10 positive cells are present in a proportion of 20% or more and 100% or less of the tissue in a serum-free medium or serum-containing medium each containing a substance capable of enhancing signal transduction mediated by Wnt and a substance inhibiting the FGF signal pathway for only a period before the appearance of a RPE65 gene-expressing cell or until RPE65 positive cells appear in the retinal tissue at a ratio of about 1% or less, followed by culturing the resulting cell aggregate in which a RPE65 gene-expressing cell does not appear or RPE65 positive cells are present in the retinal tissue at a ratio of about 1% or less in a serum-free medium or serum-containing medium each free of a substance capable of enhancing signal transduction mediated by Wnt, thereby obtaining a cell aggregate comprising a ciliary marginal zone-like structure induced to differentiate from pluripotent stem cells, or

(ii) culturing a cell aggregate comprising a retinal tissue as produced in step (B) in which Chx10 positive cells are present in a proportion of 20% or more of the tissue in a serum-free medium or serum-containing medium each containing a substance capable of enhancing signal transduction mediated by Wnt for only a period before the appearance of a RPE65 gene-expressing cell, followed by culturing the resulting cell aggregate in which a RPE65 gene-expressing cell does not appear in a serum-free medium or serum-containing medium each free of a substance capable of enhancing signal transduction mediated by Wnt, thereby obtaining a cell aggregate comprising a ciliary marginal zone-like structure induced to differentiate from pluripotent stem cells;

followed by performing step (1):

(1) dispersing (a) the cell aggregate comprising a ciliary marginal zone-like structure generated in step (i) or (ii), or (b) a ciliary marginal zone-like structure separated from the cell aggregate comprising a ciliary marginal zone-like structure generated in step (i) or (ii), followed by floating culturing the resulting dispersed cells at $1\times10^2$ cells/ml to $1\times10^6$ cells/ml in a serum-free medium, thereby obtaining a retinosphere comprising a ciliary marginal zone stem cell, wherein the ciliary marginal zone stem cell is stage specific embryonic antigen-1 positive, Rax gene positive, Chx10 gene positive, Rdh10 gene positive, Otx1 gene positive, Crx gene negative, and β-III tubulin gene negative and non-pigmented, wherein the pluripotent stem cell is a human pluripotent stem cell, and wherein the retinosphere contains 40% or more of Rax positive and stage specific embryonic antigen-1 positive cells and is free of pigment deposition.

2. The method according to claim 1, further comprising performing step (2) subsequent to performing step (1):

(2) dispersing the retinosphere obtained in step (1), followed by collecting stage specific embryonic antigen-1 positive cells from the resulting dispersed cells, thereby obtaining a stage specific embryonic antigen-1 positive cell population comprising a ciliary marginal zone stem cell.

3. The method according to claim 1, wherein the floating culturing in step (1) is performed in a serum-free medium containing one or more substances selected from the group consisting of substances capable of enhancing signal transduction mediated by FGF and substances capable of enhancing signal transduction mediated by EGF.

4. The method according to claim 3, wherein the serum-free medium further comprises a ROCK inhibitor.

5. A method according to claim 1, further comprising a step of culturing a ciliary marginal zone stem cell in the presence of one or more substances selected from the group consisting of Notch signal inhibitory substances, retinoid and taurine to produce a retinal layer-specific neuron.

6. A method according to claim 1, further comprising transplanting the ciliary marginal zone stem cell into a subject.

7. A method for producing a retinal layer-specific neuron, comprising the steps of:

(I) producing a ciliary marginal zone stem cell by the method according to claim 1, and (II) culturing the ciliary marginal zone stem cell obtained in step (I) in the presence of one or more substances selected from the group consisting of Notch signal inhibitory substances, and taurine.

8. The method according to claim 1, wherein the step (i) is performed and followed by step (1).

9. The method according to claim 1, wherein the step (ii) is performed and followed by step (1).

10. A method for producing a ciliary marginal zone stem cell, comprising:

performing steps (A) and (B):

(A) subjecting pluripotent stem cells to floating culture in a serum-free medium to form an aggregate of pluripotent stem cells, and (B) performing floating culture of the aggregate formed in step (A) in a serum-free medium or serum-containing medium each free of a substance capable of enhancing signal transduction mediated by Sonic hedgehog and containing a substance capable of enhancing signal transduction mediated by BMP to produce a cell aggregate comprising a retinal tissue, followed by performing step (i) or (ii):

(i) culturing a cell aggregate comprising a retinal tissue as produced in step (B) in which Chx10 positive cells are present in a proportion of 20% or more and 100% or less of the tissue in a serum-free medium or serum-containing medium each containing a substance capable of enhancing signal transduction mediated by Wnt and a substance inhibiting the FGF signal pathway for only a period before the appearance of a RPE65 gene-expressing cell or until RPE65 positive cells appear in the retinal tissue at a ratio of about 1% or less, followed by culturing the resulting cell aggregate in which a RPE65 gene-expressing cell does not appear or RPE65 positive cells are present in the retinal tissue at a ratio of about 1% or less in a serum-free medium or serum-containing medium each free of a substance capable of enhancing signal transduction mediated by Wnt, thereby obtaining a cell aggregate comprising a ciliary marginal zone-like structure induced to differentiate from pluripotent stem cells, or (ii) culturing a cell aggregate comprising a retinal tissue as produced in step (B) in which Chx10 positive cells are present in a proportion of 20% or more of the tissue in a serum-free medium or serum-containing medium each containing a substance capable of enhancing signal transduction mediated by Wnt for only a period before the appearance of a RPE65 gene-expressing cell, followed by culturing the resulting cell aggregate in which a RPE65 gene-expressing cell does not appear in a serum-free medium or serum-containing medium each free of a substance capable of enhancing signal transduction mediated by Wnt, thereby obtaining a cell aggregate comprising a ciliary marginal zone-like structure induced to differentiate from pluripotent stem cells, followed by performing step (1) and (2):

(1) dispersing (a) the cell aggregate comprising a ciliary marginal zone-like structure generated in step (i) or (ii), or (b) a ciliary marginal zone-like structure separated from the cell aggregate comprising a ciliary marginal zone-like structure generated in step (i) or (ii), followed by collecting stage specific embryonic antigen-1 positive cells from the resulting dispersed cells, thereby obtaining a stage specific embryonic antigen-1 positive cell population comprising a ciliary marginal zone stem cell, and (2) dispersing the stage specific embryonic antigen-1 positive cell population comprising a ciliary marginal zone stem cell generated in step (1), followed by floating culturing the resulting dispersed cells at $1\times10^2$ cells/ml to $1\times10^6$ cells/ml in a serum-free medium, thereby obtaining a retinosphere comprising a ciliary marginal zone stem cell, wherein the ciliary marginal zone stem cell is stage specific embryonic antigen-1 positive, Rax gene positive, Chx10 gene positive, Rdh10 gene positive, Otx1 gene positive, Crx gene negative and β-III tubulin gene negative and non-pigmented, wherein the pluripotent stem cell is a human pluripotent stem cell, and wherein the retinosphere contains 40% or more of Rax positive and stage specific embryonic antigen-1 positive cells and is free of pigment deposition.

11. A method according to claim 10, further comprising transplanting the ciliary marginal zone stem cell into a subject.

* * * * *